United States Patent
O'Hare et al.

(10) Patent No.: US 8,980,781 B2
(45) Date of Patent: Mar. 17, 2015

(54) CATALYSTS

(75) Inventors: Dermot O'Hare, Oxford (GB); Paul Ransom, Oxford (GB); Andrew Ashley, Oxford (GB)

(73) Assignee: Isis Innovation Limited (GB)

( * ) Notice: Subject to any disclaimer, the term of this patent is extended or adjusted under 35 U.S.C. 154(b) by 59 days.

(21) Appl. No.: 13/503,906

(22) PCT Filed: Oct. 25, 2010

(86) PCT No.: PCT/GB2010/051791
§ 371 (c)(1),
(2), (4) Date: Jul. 9, 2012

(87) PCT Pub. No.: WO2011/051705
PCT Pub. Date: May 5, 2011

(65) Prior Publication Data
US 2012/0271016 A1 Oct. 25, 2012

(30) Foreign Application Priority Data
Oct. 26, 2009 (GB) .................................. 0918736.0

(51) Int. Cl.
C07F 17/00 (2006.01)
C08F 4/642 (2006.01)
C08F 4/6592 (2006.01)
C08F 10/02 (2006.01)
C08F 110/02 (2006.01)
B01J 31/22 (2006.01)
C08F 10/00 (2006.01)
C08F 4/659 (2006.01)

(52) U.S. Cl.
CPC ............ B01J 31/2295 (2013.01); C08F 10/00 (2013.01); B01J 2231/12 (2013.01); B01J 2531/0263 (2013.01); B01J 2531/46 (2013.01); B01J 2531/48 (2013.01); B01J 2531/49 (2013.01); C08F 4/65912 (2013.01); C08F 110/02 (2013.01); Y10S 526/943 (2013.01)
USPC ............ 502/152; 502/103; 556/53; 526/160; 526/165; 526/352; 526/943

(58) Field of Classification Search
CPC .. C08F 17/00; C08F 4/65912; C08F 4/65927; C08F 2420/00; C08F 10/02
USPC ............ 556/53; 502/103, 152; 526/160, 165, 526/943, 352
See application file for complete search history.

(56) References Cited

U.S. PATENT DOCUMENTS

| 5,672,668 A | 9/1997 | Winter et al. |
| 6,583,238 B1 | 6/2003 | Gores et al. |

FOREIGN PATENT DOCUMENTS

| CA | 2133181 | 3/1995 |
| EP | 0645401 | 9/1994 |
| WO | WO98/46616 | 10/1998 |
| WO | WO9843989 | 10/1998 |
| WO | WO00/26266 | 5/2000 |

OTHER PUBLICATIONS

PCT Search Report/Written Opinion prepared for PCT/GB2010/0051791, mailed Feb. 7, 2011.
GB Search Report prepared for GB0918736.0, prepared Mar. 22, 2010.

*Primary Examiner* — Caixia Lu
(74) *Attorney, Agent, or Firm* — Barnes & Thornburg LLP

(57) ABSTRACT

The present invention relates to novel metallocene catalysts of formula I, which is defined herein. The present invention also provides processes for making these catalysts and their use in olefin polymerisation reactions.

10 Claims, 4 Drawing Sheets

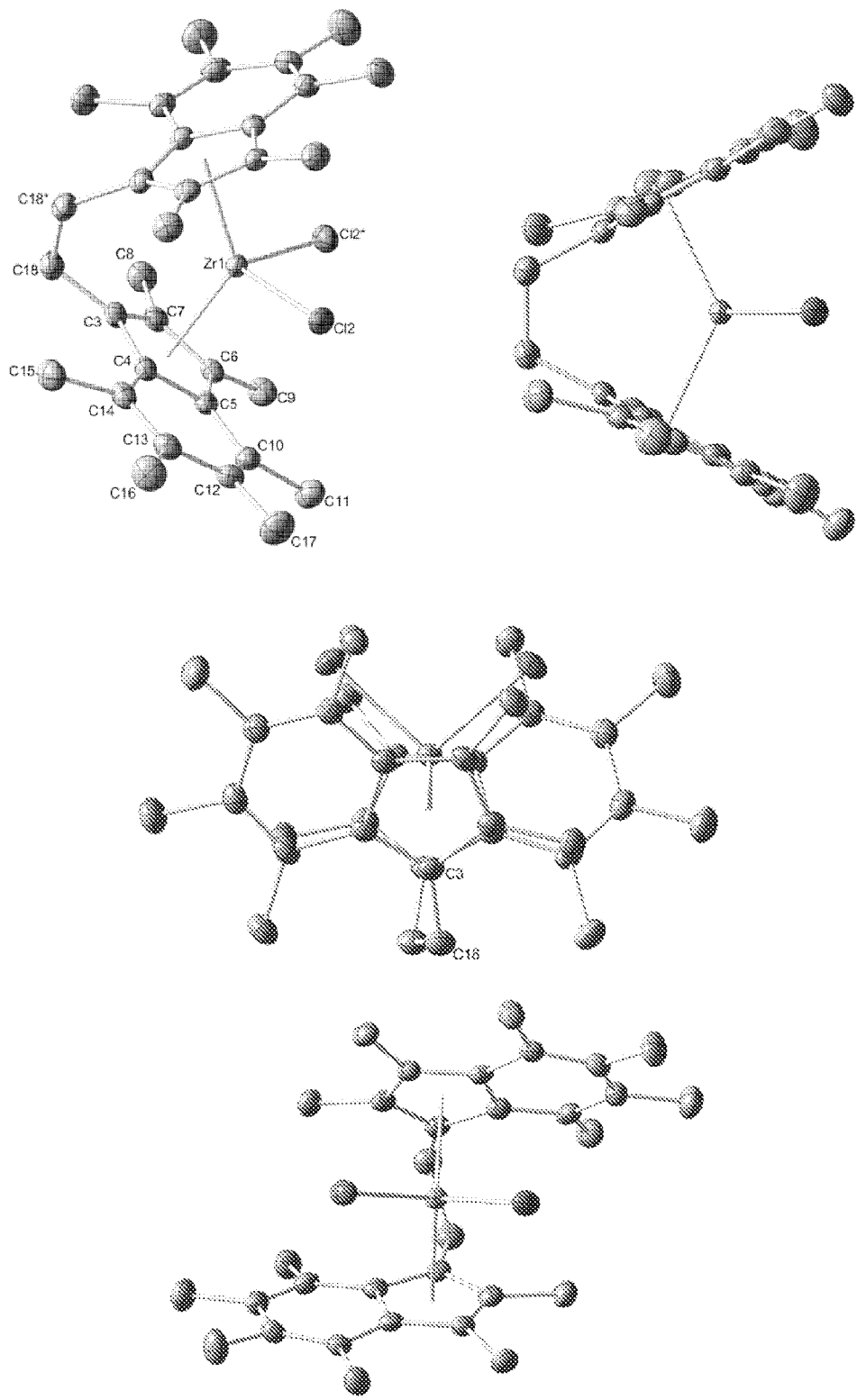
Figure 1: Four views of *rac*-EBI*ZrCl$_2$, with H atoms omitted for clarity and thermal ellipsoids drawn at 50%

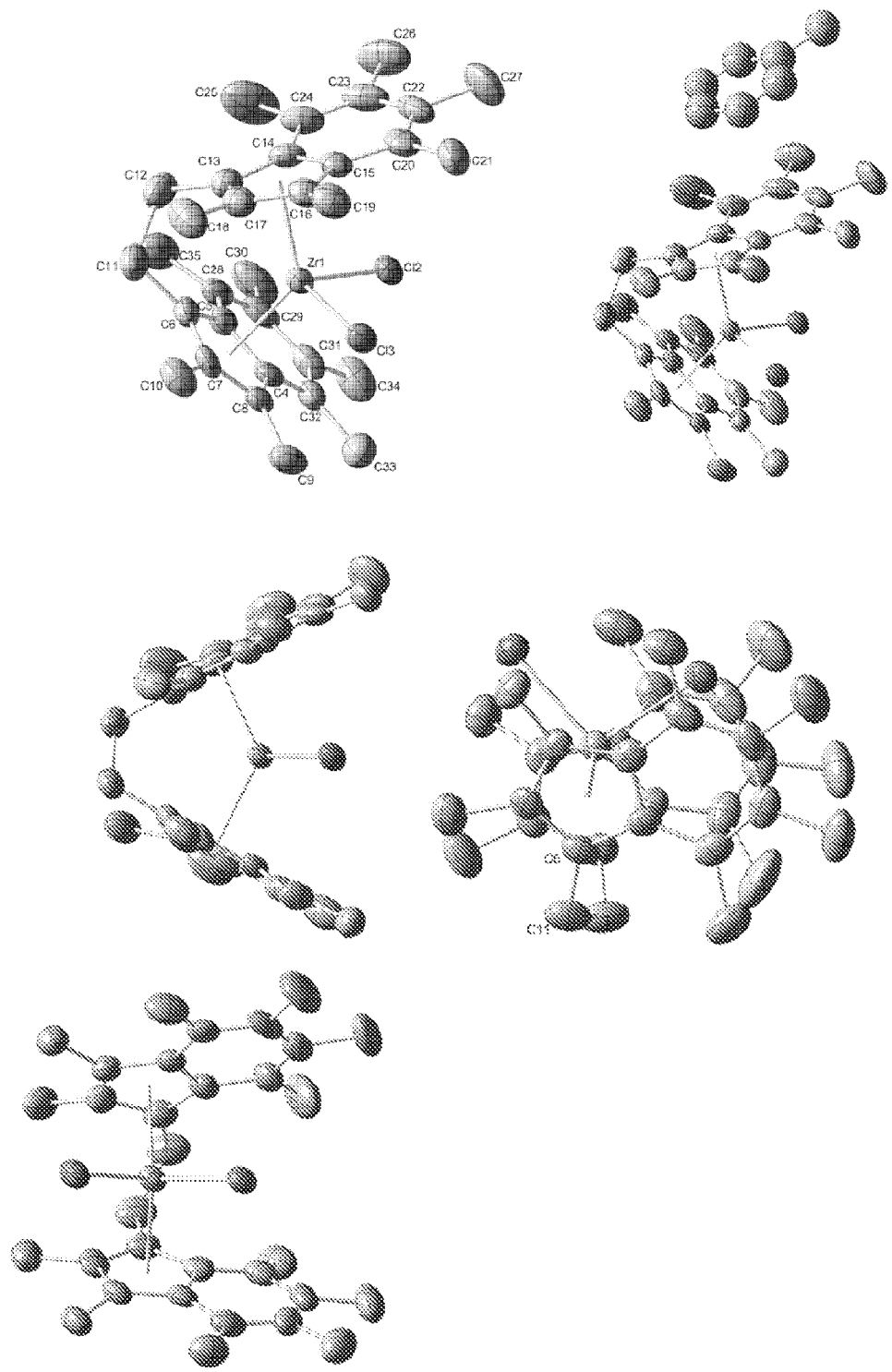
Figure 2: Alternate views of *meso*-EBI*ZrCl₂, with H atoms and toluene molecule omitted for clarity; second view shows the location of the toluene molecule. Thermal ellipsoids are drawn at 50%

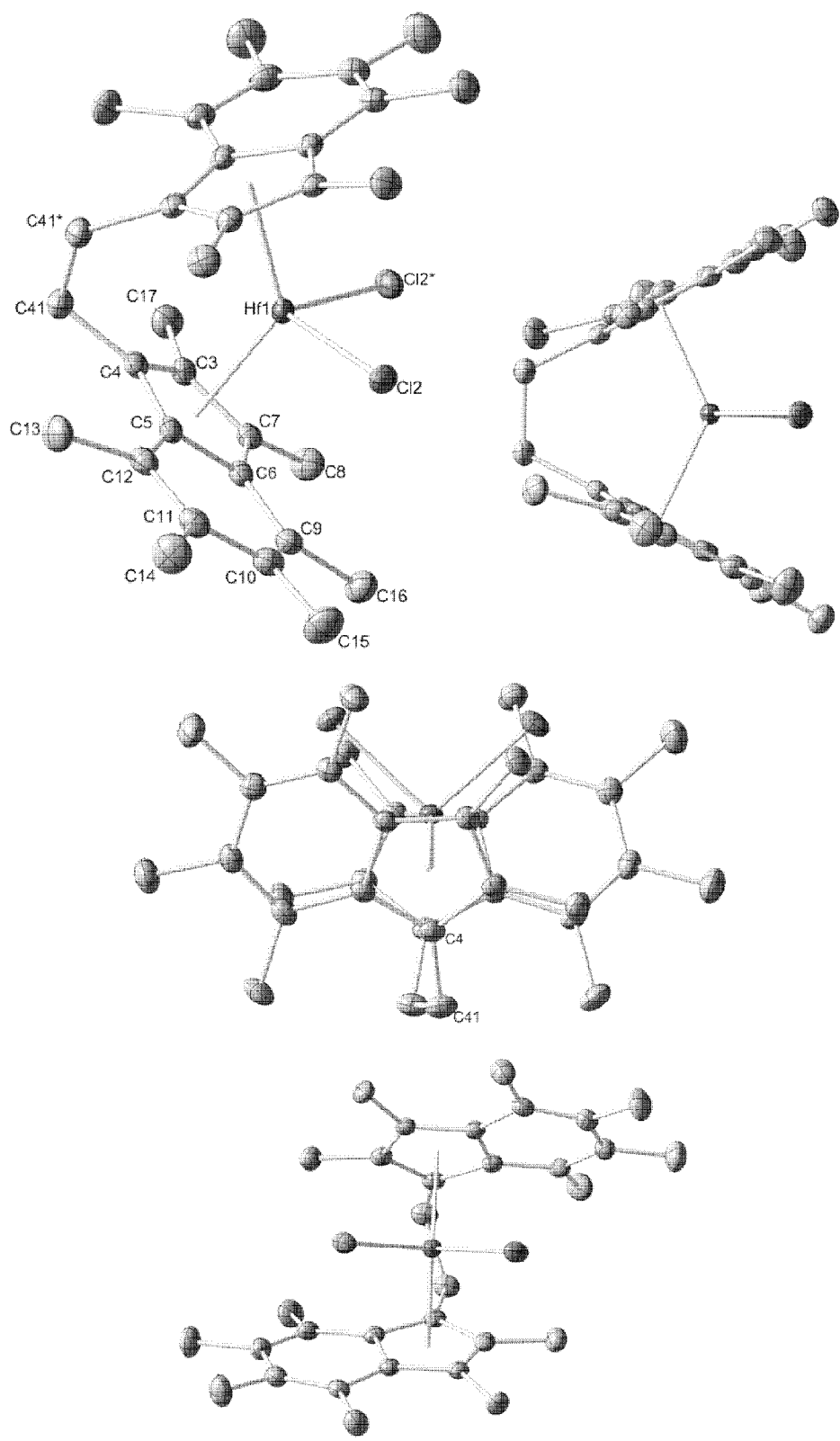
Figure 3: Four views of *rac*-EBI*HfCl₂, with H atoms omitted for clarity and thermal ellipsoids drawn at 50%

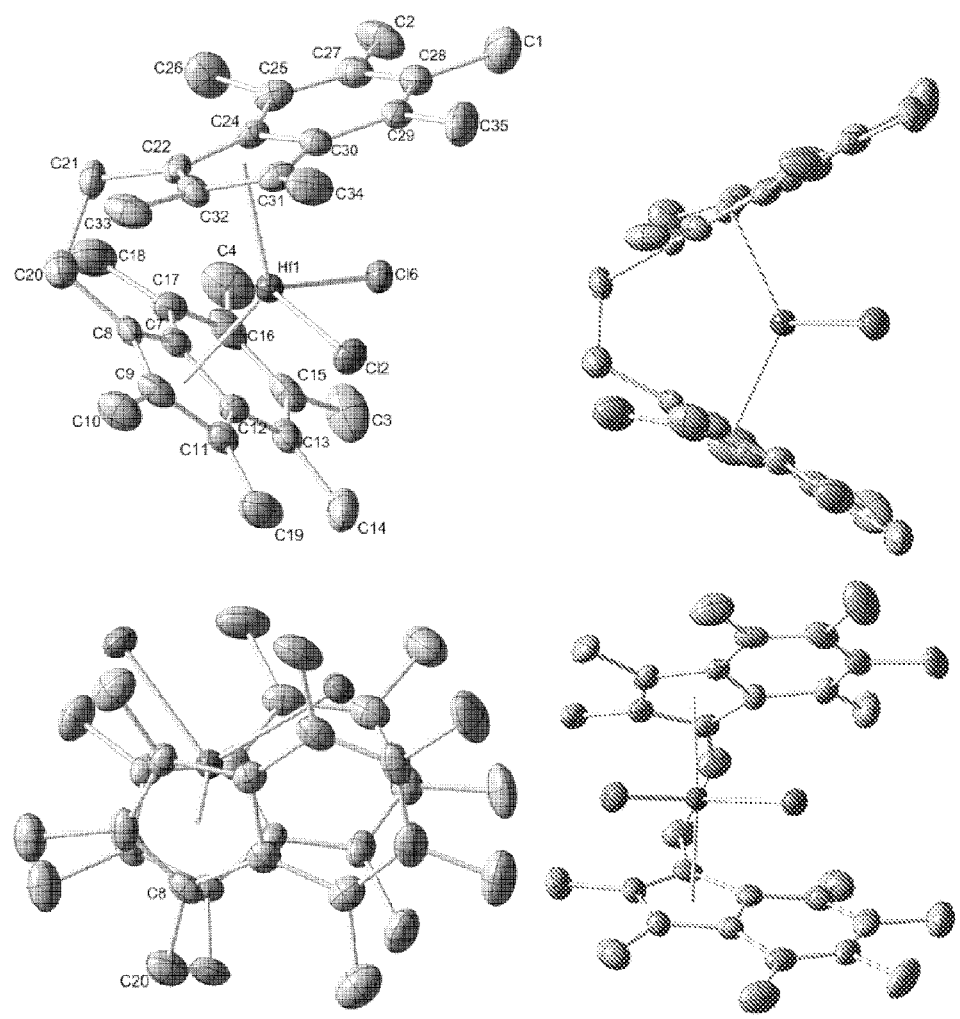
Figure 4: Four views of *meso*-EBI*HfCl$_2$, with H atoms omitted for clarity and thermal ellipsoids drawn at 50%

CATALYSTS

CROSS-REFERENCE TO RELATED APPLICATIONS

This application is a U.S. national counterpart application of PCT International Application Serial No. PCT/GB2010/051791, filed Oct. 25, 2010, which claims priority to GB Patent Application Serial Number 0918736.0, filed Oct. 26, 2009, the entire disclosures of both which Applications are hereby incorporated herein by reference.

TECHNICAL FIELD

This invention relates to catalysts. More specifically, the present invention relates to particular metallocene procatalysts, and the use of such procatalysts in polyolefin polymerization reactions.

BACKGROUND

It is well known that ethylene (and α-olefins in general) can be readily polymerized at low or medium pressures in the presence of certain transition metal catalysts. These catalysts are generally known as Zeigler-Natta type catalysts.

A particular group of these Zeigler-Natta type catalysts, which catalyse the polymerization of ethylene (and α-olefins in general), comprise an aluminoxane activator and a metallocene transition metal catalyst. Metallocenes comprise a metal bound between two $\eta^5$-cyclopentadienyl type ligands. Generally the $\eta^5$-cyclopentadienyl type ligands are selected from $\eta^5$-cyclopentadienyl, $\eta^5$-indenyl and $\eta^5$-fluorenyl.

It is also well known that these $\eta^5$-cyclopentadienyl type ligands can be modified in a myriad of ways. One particular modification involves the introduction of a linking group between the two cyclopentadienyl rings to form ansa-metallocenes.

Numerous ansa-metallocenes of transition metals are known in the art. However, there remains a need for improved ansa-metallocene catalysts for use in polyolefin polymerization reactions. In particular, there remains a need for new metallocene catalysts with high polymerization activities/efficiencies.

There is also a need for catalysts that can produce polyethylenes with particular characteristics. For example, catalysts capable of producing linear high density polyethylene (LHDPE) with a relatively narrow dispersion in polymer chain length are desirable.

Accordingly, it is an object of the present invention to provide improved ansa-metallocene catalysts.

BRIEF SUMMARY OF THE DISCLOSURE

In a first aspect, the present invention provides a compound of the formula I shown below

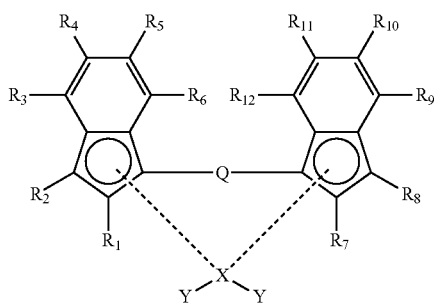

I wherein:
$R_1, R_2, R_3, R_4, R_5, R_6, R_7, R_8, R_9, R_{10}, R_{11}$ and $R_{12}$ are each independently selected from hydrocarbyl, carbocyclyl or heterocyclyl, each of which is optionally substituted;
Q is a bridging group;
X is selected from zirconium, titanium or hafnium;
Y is selected from halo, hydride, a phosphonated or sulfonated anion, or a (1-6C)alkyl, (1-6C)alkoxy, aryl or aryloxy group which is optionally substituted with halo, nitro, amino, phenyl, (1-6C)alkoxy, or Si[(1-4C)alkyl]$_3$.

It has surprisingly been found that the compounds of the present invention possess particularly high catalytic performance when used for the polymerization of polyethylene.

In a further aspect, the present invention provides a process for synthesizing a compound of formula I as defined herein.

In a further aspect, the present invention provides the use of a compound of formula I as defined herein as a procatalyst for the synthesis of polyolefins (e.g. polyethylene).

In a further aspect, the present invention provides a process for the polymerization of olefin monomers (e.g. ethylene) comprising reacting the olefin monomers in the presence of a compound of formula I as defined herein and suitable activator.

BRIEF DESCRIPTION OF THE DRAWINGS

FIG. 1 shows four views of rac-EBI*ZrCl$_2$, with H atoms omitted for clarity and thermal ellipsoids drawn at 50%;

FIG. 2 shows alternate views of meso-EBI*ZrCl$_2$, with H atoms and toluene molecule omitted for clarity and thermal ellipsoids drawn at 50% (second view shows the location of the toluene molecule);

FIG. 3 shows four views of rac-EBI*HfCl$_2$, with H atoms omitted for clarity and thermal ellipsoids drawn at 50%; and FIG. 4 shows four views of meso-EBI*HfCl$_2$, with H atoms omitted for clarity and thermal ellipsoids drawn at 50%.

DETAILED DESCRIPTION

Definitions

Hydrocarbyl

The term "hydrocarbyl" as used herein includes reference to moieties consisting exclusively of hydrogen and carbon atoms; such a moiety is an aliphatic moiety. The moiety may, for example, comprise 1, 2, 3, 4, 5, 6, 7, 8, 9, 10, 11 or 12 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); alkenyl (e.g. 2-butenyl); and alkynyl (e.g. 2-butynyl) and the like.

Alkyl

The term "alkyl" as used herein include reference to a straight or branched chain alkyl moieties, typically having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, an alkyl may have 1, 2, 3 or 4 carbon atoms.

Alkoxy

The term "alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9 or 10 ring carbon atoms. In particular, carbocyclyl includes a 3- to 10-membered ring or ring system and, in particular, a 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, naphthyl, and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9 or 10 ring carbon atoms. Aryl is often phenyl but may be a polycyclic ring system, having two or more rings, at least one of which is aromatic. This term includes reference to groups such as phenyl, naphthyl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9 or 10 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heteroaryl

The term "heteroaryl" as used herein includes reference to an aromatic heterocyclic ring system having 5, 6, 7, 8, 9 or 10 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" or "halo" as used herein includes reference to F, Cl, Br or I. In an embodiment, a halogen is F, Cl or Br. In many instances, a halogen will be Cl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Catalytic Compounds

As stated above, the present invention provides a compound of the formula I shown below

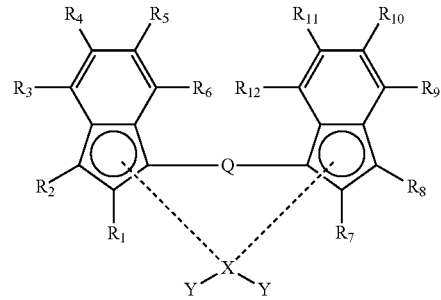

I wherein:
$R_1, R_2, R_3, R_4, R_5, R_6, R_7, R_8, R_9, R_{10}, R_{11}$ and $R_{12}$ are each independently selected from hydrocarbyl, carbocyclyl or heterocyclyl, each of which is optionally substituted;
Q is a bridging group;
X is selected from zirconium, titanium or hafnium; and
each Y is selected from halo, hydride, a phosphonated or sulfonated anion, or a (1-6C)alkyl, (1-6C)alkoxy, aryl or aryloxy group which is optionally substituted with halo, nitro, amino, phenyl, (1-6C)alkoxy, or $Si[(1-4C)alkyl]_3$.

It will be appreciated that the structural formula I presented above is intended to show the substituent groups in a clear manner. A more representative illustration of the spatial arrangement of the groups is shown in the alternative representation below:

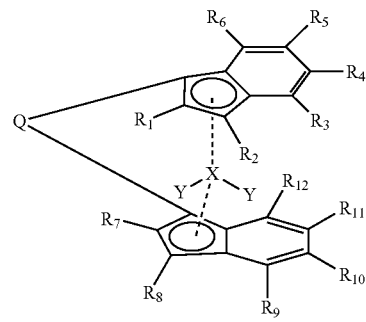

In an embodiment, $R_1, R_2, R_3, R_4, R_5, R_6, R_7, R_8, R_9, R_{10}$, $R_{11}$ and $R_{12}$ are each independently selected from a hydrocarbyl, carbocyclyl or heterocyclyl group, each of which is optionally substituted by halo, amino, nitro, cyano, (1-6C)alkyl, (1-6C)alkoxy, (1-6C)alkylamino, [(1-6C)alkyl]$_2$amino, or —S(O)$_r$(1-6C)alkyl (where r is 0, 1 or 2).

In an embodiment, $R_1$, $R_2$, $R_3$, $R_4$, $R_5$, $R_6$, $R_7$, $R_8$, $R_9$, $R_{10}$, $R_{11}$ and $R_{12}$ are each independently selected from a hydrocarbyl or aryl group, each of which is optionally substituted by halo, amino, nitro, cyano, (1-6C)alkyl, (1-6C)alkoxy, (1-6C)alkylamino, [(1-6C)alkyl]$_2$amino, or —S(O)$_r$(1-6C)alkyl (where r is 0, 1 or 2).

In an embodiment, $R_1$, $R_2$, $R_3$, $R_4$, $R_5$, $R_6$, $R_7$, $R_8$, $R_9$, $R_{10}$, $R_{11}$ and $R_{12}$ are each independently selected from (1-6C)alkyl or phenyl, each of which is optionally substituted by halo, amino, nitro, cyano, (1-6C)alkyl, (1-6C)alkoxy, (1-6C)alkylamino, [(1-6C)alkyl]$_2$amino, or —S(O)$_r$(1-6C)alkyl (where r is 0, 1 or 2).

In an embodiment, $R_1$, $R_2$, $R_3$, $R_4$, $R_5$, $R_6$, $R_7$, $R_8$, $R_9$, $R_{10}$, $R_{11}$ and $R_{12}$ are (1-6C)alkyl groups that are optionally substituted by halo, amino, nitro, cyano, (1-6C)alkyl, (1-6C)alkoxy, (1-6C)alkylamino, [(1-6C)alkyl]$_2$amino, or —S(O)$_r$(1-6C)alkyl (where r is 0, 1 or 2).

In an embodiment, $R_1$, $R_2$, $R_3$, $R_4$, $R_5$, $R_6$, $R_7$, $R_8$, $R_9$, $R_{10}$, $R_{11}$ and $R_{12}$ are (1-6C)alkyl.

In an embodiment, $R_1$, $R_2$, $R_3$, $R_4$, $R_5$, $R_6$, $R_7$, $R_8$, $R_9$, $R_{10}$, $R_{11}$ and $R_{12}$ are (1-4C)alkyl.

In an embodiment, $R_1$, $R_2$, $R_3$, $R_4$, $R_5$, $R_6$, $R_7$, $R_8$, $R_9$, $R_{10}$, $R_{11}$ and $R_{12}$ are (1-2C)alkyl.

In an embodiment, $R_1$, $R_2$, $R_3$, $R_4$, $R_5$, $R_6$, $R_7$, $R_8$, $R_9$, $R_{10}$, $R_{11}$ and $R_{12}$ are all methyl.

In an embodiment, $R_1$ and $R_7$, $R_2$ and $R_8$, $R_3$ and $R_9$, $R_4$ and $R_{10}$, $R_5$ and $R_{11}$, and $R_6$ and $R_{12}$ are the same.

Suitably, Q is a bridging group comprising 1, 2 or 3 bridging atoms selected from C, N, O, S, Ge, Sn, P, B or Si, or a suitable combination thereof. The bridging group Q may also optionally bear one or more substituent groups, for example, one or more hydroxyl, (1-6C)alkyl, (1-6C)alkoxy or aryl groups.

Suitably Q is a group of the formula —[C(R$^a$R$^b$)]$_n$— wherein n is 2 or 3 and R$^a$ and R$^b$ are each independently hydrogen, (1-6C)alkyl or (1-6C)alkoxy.

In an embodiment, Q is —CH$_2$—CH$_2$— or —CH$_2$—CH$_2$—CH$_2$—.

In a particular embodiment, Q is —CH$_2$—CH$_2$—.

In an embodiment, X is zirconium or hafnium.

In a particular embodiment, X is zirconium.

In a particular embodiment, X is hafnium.

In an embodiment, each Y group is the same.

In an embodiment, Y is selected from halo, (1-6C)alkyl or phenyl, wherein the alkyl or phenyl group is optionally substituted with halo, nitro, amino, phenyl, (1-6C)alkoxy, or Si[(1-4C)alkyl]$_3$.

In an embodiment, Y is selected from halo or a (1-6C)alkyl group which is optionally substituted with halo, nitro, amino, phenyl, (1-6C)alkoxy, or Si[(1-4C)alkyl]$_3$.

In another embodiment, Y is selected from halo or a (1-6C) alkyl group which is optionally substituted with halo, phenyl, or Si[(1-2C)alkyl]$_3$.

In another embodiment, Y is selected from chloro, bromo, or a (1-4C)alkyl group which is optionally substituted with halo, phenyl, or Si[Me]$_3$.

In a particular embodiment, Y is selected from chloro or a (1-4C)alkyl group which is optionally substituted with phenyl or Si[Me]$_3$.

In a further embodiment, Y is chloro, bromo or methyl.

In a further embodiment, Y is chloro or bromo.

In a further embodiment, Y is chloro.

In another embodiment, Y is methyl.

In an embodiment, the compound of the present invention has the structural formula II shown below

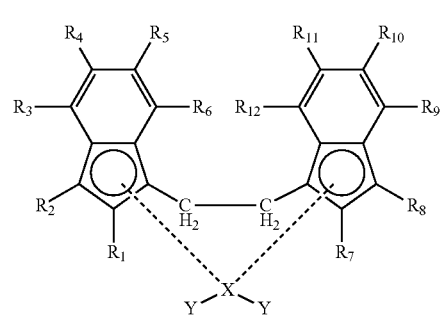

wherein:
$R_1$, $R_2$, $R_3$, $R_4$, $R_5$, $R_6$, $R_7$, $R_8$, $R_9$, $R_{10}$, $R_{11}$, $R_{12}$, X and Y are each as defined hereinbefore.

In an embodiment, the compound of the present invention has the structural formula III shown below

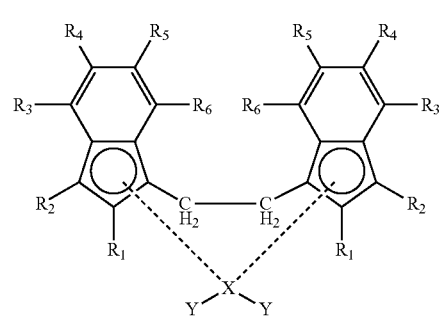

wherein:
$R_1$, $R_2$, $R_3$, $R_4$, $R_5$, $R_6$, X and Y are each as defined hereinbefore.

In an embodiment, the compound has the structural formula IV shown below

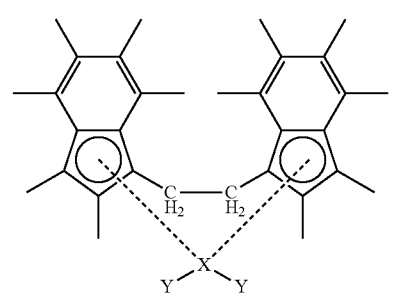

wherein:
X and Y are as defined hereinbefore.

In a particular group of compounds of formula IV, X is zirconium or hafnium.

In a further group of compounds of formula IV, X is zirconium.

In a further group of compounds of formula IV, X is hafnium.

In a particular group of compounds of formula IV, each Y group is the same.

In a further group of compounds of formula IV, Y is selected from halo, (1-6C)alkyl or phenyl, wherein the alkyl or phenyl group is optionally substituted with halo, nitro, amino, phenyl, (1-6C)alkoxy, or Si[(1-4C)alkyl]$_3$.

In a further group of compounds of formula IV, Y is selected from halo or a (1-6C)alkyl group which is optionally substituted with halo, phenyl or Si[(1-2C)alkyl]$_3$.

In a particular group of compounds of formula IV, Y is selected from chloro, bromo or a (1-4C)alkyl group which is optionally substituted with halo, phenyl or Si[Me]$_3$.

In a particular group of compounds of formula IV, Y is selected from chloro or a (1-4C)alkyl group which is optionally substituted with halo, phenyl, or Si[Me]$_3$.

In a particular group of compounds of formula IV, Y is chloro, bromo or methyl, especially chloro or methyl.

In an embodiment, the compound has the structural formula V shown below

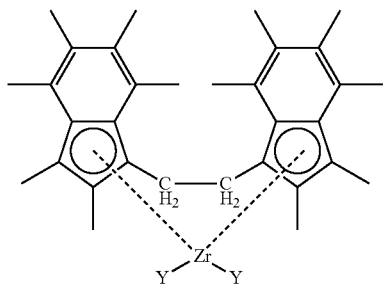

V wherein:
Y is as defined hereinbefore.

In an embodiment, the compound has the structural formula VI shown below

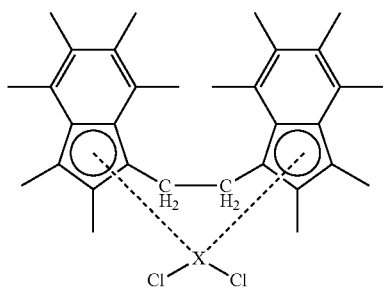

VI wherein:
X is as defined hereinbefore.

A particular compound of the invention is:

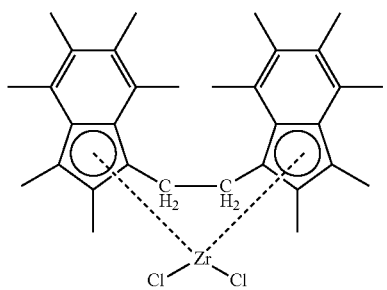

Particular examples of catalytic compounds of the invention include any one of the following:
EBI*ZrCl$_2$;
EBI*HfCl$_2$;
EBI*TiCl$_2$;
EBI*ZrMe$_2$;
EBI*Zr(CH$_2$R)$_2$ (where R is phenyl, tertiary butyl or trimethylsilane);
EBI*HfMe$_2$; or
EBI*Hf(CH$_2$R)$_2$ (where R is phenyl, tertiary butyl or trimethylsilane).
and wherein EBI* is ethylene-bis-hexamethylindenyl.

The compounds of the present invention may be present in one or more isomeric forms. In particular, the compounds of the present invention may be present as meso or rac isomers, and the present invention includes both such isomeric forms. A person skilled in the art will appreciate that a mixture of isomers of the compound of the present invention may be used for catalysis applications, or the isomers may be separated and used individually (using techniques well known in the art, such as, for example, fractional crystallization).

Synthesis

The compounds of the present invention may be synthesised by any suitable process known in the art. Particular examples of processes for the preparing compounds of the present invention are set out in the accompanying examples.

Suitably, a compound of the present invention is prepared by:
(i) reacting a compound of formula A:

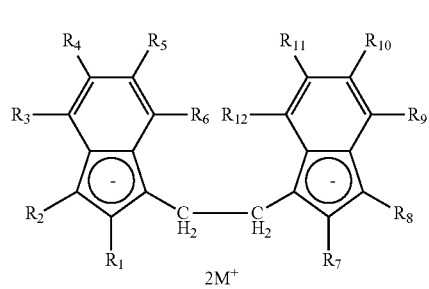

A (wherein $R_1$, $R_2$, $R_3$, $R_4$, $R_5$, $R_6$, $R_7$, $R_8$, $R_9$, $R_{10}$, $R_{11}$, and $R_{12}$ are each as defined hereinbefore and M is Li, Na or K)
with a compound of the formula B:

$$X(Y')_4 \qquad B$$

(wherein X is as defined hereinbefore and Y' is halo (particularly chloro or bromo)) in the presence of a suitable solvent to form a compound of formula Ia:

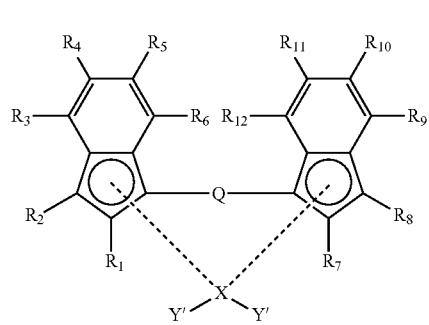

Ia and optionally thereafter:

(ii) reacting the compound of formula Ia above with MY" (wherein M is as defined above and Y" is a group Y as defined herein other than halo), in the presence of a suitable solvent to form the compound of the formula Ib shown below

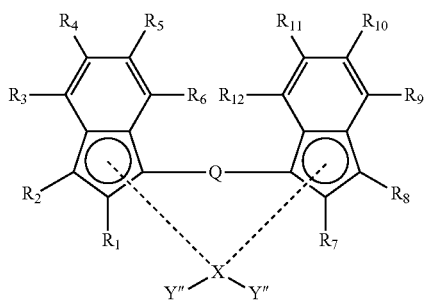

Ib

Suitably, M is Li in step (i) of the process defined above.

Suitably, the compound of formula B is provided as a solvate. In particular, the compound of formula B may be provided as $X(Y')_4 \cdot THF_p$, where p is an integer (e.g. 2).

Any suitable solvent may be used for step (i) of the process defined above. A particularly suitable solvent is toluene or THF.

If a compound of formula I in which Y is other than halo is required, then the compound of formula Ia above may be further reacted in the manner defined in step (ii) to provide a compound of formula Ib.

Any suitable solvent may be used for step (ii) of the process defined above. A suitable solvent may be, for example, diethyl ether, toluene, THF, dichloromethane, chloroform, hexane DMF, benzene etc.

Processes by which compounds of the formula A above can be prepared are well known art. For example, a process for the synthesis of a di-sodium ethylene-bis-hexamethylindenyl ligand of formula A is described in J. Organomet. Chem., 694, (2009), 1059-1068. A process for the synthesis of a di-lithium ethylene-bis-hexamethylindenyl ligand of formula A is described in the accompanying examples.

Compounds of formula A in which $R_1$ and $R_7$, $R_2$ and $R_8$, $R_3$ and $R_9$, $R_4$ and $R_{10}$, $R_5$ and $R_{11}$, $R_6$ and $R_{12}$ are the same, and Q is —CH$_2$—CH$_2$— may generally be prepared by:

(i) Reacting a compound of formula D

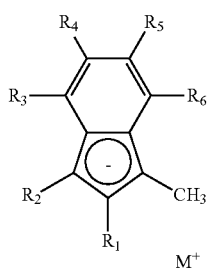

D (wherein M is lithium, sodium, or potassium; and $R_1$, $R_2$, $R_3$, $R_4$, $R_5$ and $R_6$ are as defined hereinbefore) with BrCN in the presence of a suitable solvent to form a compound of formula E shown below

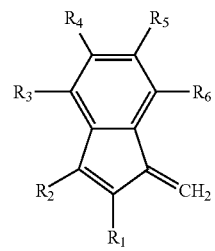

E and (ii) reacting a compound of formula E with $C_{10}H_8 \cdot M$ in the presence of a suitable solvent to form a compound of formula A.

Compounds of formula D can be readily synthesized by techniques well known in the art.

Any suitable solvent may be used for step (i) of the above process. A particularly suitable solvent is diethyl ether.

Similarly, any suitable solvent may be used for step (ii) of the above process. A suitable solvent may be, for example, toluene, THF, DMF etc.

For the avoidance of doubt, the $C_{10}H_8 \cdot M$ reagent used in step (ii) of the above process is lithium, sodium or potassium naphthalenide. In an embodiment, $C_{10}H_8 \cdot M$ is sodium naphthalenide.

Applications

As previously indicated, the compounds of the present invention are extremely effective procatalysts for use in olefin polymerization reactions.

Thus, the present invention also provides the use of a compound of formula I as defined herein as an olefin polymerization procatalyst, in particular an ethylene polymerization catalyst.

The present invention also provides a process for forming a polyolefin (e.g. polyethylene) which comprises reacting the olefin monomers in the presence of a compound of formula I as defined herein and a suitable activator.

Suitable activators are well known in the art and include, but are not limited to, aluminoxanes (e.g. methylaluminoxane) or triethylaluminium.

The catalyst compound of formula I may be applied to a suitable support. Examples of suitable supports include silica gels, aluminium oxides, or any other inorganic support materials.

It is possible to pre-activate the catalyst of formula I by mixing the catalyst with the activator before use in the polymerisation reaction. Suitably, such pre-activation is carried out in solution, and typically in an inert hydrocarbon such as toluene.

Typically, the polymerisation reaction is carried out in a known manner in solution, in suspension or in the gas phase, continuously, or batchwise in one or more steps.

A person skilled in the art of olefin polymerization will be able to select suitable reaction conditions (e.g. temperature, pressures, reaction times etc.) for such a polymerization reaction. A person skilled in the art will also be able to manipulate the process parameters in order to produce a polyolefin having particular properties. For example, the temperature of such reactions could range from −60 to 250° C. and the pressures may range from 0.5 to 100 bar, in certain circumstances.

In a particular embodiment, the polyolefin is polyethylene.

EXAMPLES

The invention will now be described in more detail in relation to the following illustrative examples.

General Methodology

All organometallic manipulations were performed under an atmosphere of $N_2$ using standard Schlenk line techniques or a MBraun UNIlab glovebox, unless stated otherwise. All organic reactions were carried out under air unless stated otherwise. Solvents used were dried by either reflux over sodium-benzophenone diketyl (THF), or passage through activated alumina (hexane, $Et_2O$, toluene, $CH_2Cl_2$) using a MBraun SPS-800 solvent system. Solvents were stored in dried glass ampoules, and thoroughly degassed by passage of a stream of $N_2$ gas through the liquid and tested with a standard sodium-benzophenone-THF solution before use. Deuterated solvents for NMR spectroscopy of oxygen or moisture sensitive materials were treated as follows: $C_6D_6$ was freeze-pump-thaw degassed and dried over a K mirror; $d^5$-pyridine and $CDCl_3$ were dried by reflux over calcium hydride and purified by trap-to-trap distillation; and $CD_2Cl_2$ was dried over 3 Å molecular sieves.

$^1H$ and $^{13}C$ NMR spectroscopy were performed using a Varian 300 MHz spectrometer and recorded at 300 K unless stated otherwise. $^1H$ and $^{13}C$ NMR spectra were referenced via the residual protio solvent peak. Oxygen or moisture sensitive samples were prepared using dried and degassed solvents under an inert atmosphere in a glovebox, and were sealed in Wilmad 5 mm 505-PS-7 tubes fitted with Young's type concentric stopcocks.

Mass spectra were using a Bruker FT-ICR-MS Apex III spectrometer.

For Single-crystal X-ray diffraction in each case, a typical crystal was mounted on a glass fibre using the oil drop technique, with perfluoropolyether oil and cooled rapidly to 150 K in a stream of $N_2$ using an Oxford Cryosystems Cryostream.[21] Diffraction data were measured using an Enraf-Nonius KappaCCD diffractometer (graphite-monochromated MoKα radiation, λ=0.71073 Å). Series of ω-scans were generally performed to provide sufficient data in each case to a maximum resolution of 0.77 Å. Data collection and cell refinement were carried out using DENZO-SMN.[22] Intensity data were processed and corrected for absorption effects by the multi-scan method, based on multiple scans of identical and Laue equivalent reflections using SCALEPACK (within DENZO-SMN). Structure solution was carried out with direct methods using the program SIR92[23] within the CRYSTALS software suite.[24] In general, coordinates and anisotropic displacement parameters of all non-hydrogen atoms were refined freely except where this was not possible due to the presence of disorder (i.e. toluene of crystallization in meso-2). Hydrogen atoms were generally visible in the difference map and were treated in the usual manner[25].

Polymerization trials and differential scanning calorimetry (DSC) experiments were run under industrial conditions. High temperature gel permeation chromatography were performed using a Polymer Laboratories GPC220 instrument, with one PLgel Olexis guard plus two Olexis 30 cm×13 μm columns. The solvent used was 1,2,4-trichlorobenzene with anti-oxidant, at a nominal flow rate of 1.0 $mLmin^{-1}$ and nominal temperature of 160° C. Refractive index and Viscotek differential pressure detectors were used. The data were collected and analysed using Polymer Laboratories "Cirrus" software. A single solution of each sample was prepared by adding 15 mL of solvent to 15 mg of sample and heating at 190° C. for 20 minutes, with shaking to dissolve. The sample solutions were filtered through a glass-fibre filter and part of the filtered solutions were then transferred to glass sample vials. After an initial delay of 30 minutes in a heated sample compartment to allow the sample to equilibrate thermally, injection of part of the contents of each vial was carried out automatically. The samples appeared to be completely soluble and there were no problems with either the filtration or the chromatography of the solutions. The GPC system was calibrated with Polymer Laboratories polystyrene calibrants. The calibration was carried out in such a manner that combined GPC-viscosity could be used to give 'true' molecular weight data and conventional GPC could also be applied. For the conventional GPC results, the system is calibrated with linear polyethylene or linear polypropylene. This correction has previously been shown to give good estimates of the true molecular weights for the linear polymers.

For the GPC-viscosity approach, the system is still calibrated using polystyrene but the use of the refractive index (concentration) and differential pressure (viscosity) detector responses, together with accurate knowledge of the polymer solution concentration, allows computation of 'true' molecular weight data without applying any correction. This approach also gives intrinsic viscosity data that allows comparison of long chain branching. Although this approach does give 'true' molecular weight data, some parameters are adjusted to ensure a good match for a known material and the approach used to obtain the polymer sample concentration can be important. For this work, the differential refractive index (dn/dc) for the polyethylene/solvent combination was assumed and the concentration back calculated from the refractive index detector response. If samples were not simply polyethylene, errors would be introduced due to a change in dn/dc. The differential pressure (viscosity) detector response is a function of concentration and intrinsic viscosity (effective molecular weight) and the response to the propylene oligomer was too low for the application of the GPC-viscosity approach to be sensible.

Intermediate Preparation

Preparation of ethylene-bis-hexamethylindenyl, EBI*$Li_2$.$THF_{0.38}$; 1

Li (0.13 g, 1.86×$10^{-2}$ mol) and naphthalene (2.56 g, 2.00×$10^{-2}$ mol) were stirred in THF, forming a green solution after 3 hours which still contained Li and so was stirred for a further 15 hours. $C_{16}H_{20}$ (3.69 g, 1.74×$10^{-2}$ mol) was dissolved in THF giving a bright yellow solution, which was added to the dark green $C_{10}H_8Li$ mixture at −78° C. The reaction mixture was stirred at −78° C. for 30 minutes then allowed to warm to room temperature with stirring. A precipitate formed after 2 hours, and after a further 3 hours the solvent was removed under vacuum from the yellow-green mixture. The residue was washed with $Et_2O$ and dried to yield an off white powder. Yield: 3.78 g, 93%. Analysis by NMR spectroscopy showed this solid to be of the formula EBI*$Li_2$.$THF_{0.38}$, $^1H$ NMR ($d^5$-pyridine): δ 2.42, 2.45, 2.62, 2.89, 2.91 3.06 (all s, 6H, Me), 3.78 (s, 4H, $C_2H_4$). $^{13}C$ NMR ($d^5$-pyridine): δ 13.8, 16.3, 17.3, 17.4, 18.7, 19.2 (Me), 36.4 ($C_2H_4$), 97.8, 105.6, 119.1, 119.4, 123.5, 123.6, 124.8, 126.8, 128.8 (ring Cs).

Preparation of disodium ethylene-bis-hexamethylindenyl (EBI*$Na_2$)

Scheme 1: general reaction scheme

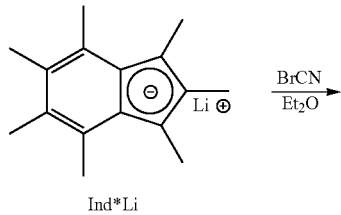

Ind*Li

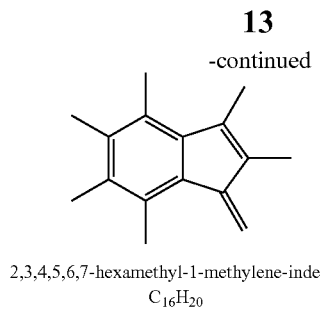

2,3,4,5,6,7-hexamethyl-1-methylene-indene, $C_{16}H_{20}$

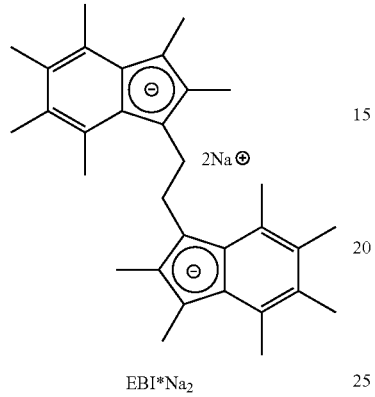

EBI*Na$_2$ (i) Synthesis of 2,3,4,5,6,7-hexamethyl-1-methylene-indene, $C_{16}H_{20}$ BrCN (2.89 g, 2.72×10$^{-3}$ mol) was added under a N$_2$ flush to a −78° C. slurry in Et$_2$O of Ind*Li (6.00 g, 2.72×10$^{-3}$ mol), prepared by a literature procedure.[1] The reaction mixture was stirred at −78° C. for 2 hours then allowed to warm to room temperature, upon which the off-white precipitate dissolved to give a yellow solution. After stirring for 15 hours under a dynamic pressure of N$_2$ to allow venting of HCN produced, volatiles were removed under vacuum. NMR analysis of the residues occasionally showed contamination of the desired product with an intermediate species, Ind*Br. Addition of Et$_3$N and further stirring converted this into the fulvene compound $C_{16}H_{20}$. Extraction with 30° C. pentane, passing the resulting solution through silica and removal of the solvent under vacuum afforded 2,3,4,5,6,7-hexamethyl-1-methylene-indene, $C_{16}H_{20}$ as a bright yellow solid. Yield: 4.10 g, 71%.

Characterising Data:
$^1$H NMR (C$_6$D$_6$) δ (ppm): 1.91, 2.08 (both s, 3H, Me), 2.11 (s, 6H, Me), 2.30, 2.36 (both s, 3H, Me), 5.56, 5.84 (both s, 1H, CH$_2$).
$^1$H NMR (CDCl$_3$) δ (ppm): 2.00, 2.23, 2.26, 2.28 (all s, 3H, Me), 2.45 (bs, 6H, Me), 5.51, 5.88 (both s, 1H, CH$_2$).
$^{13}$C NMR(C$_6$D$_6$) δ (ppm): 9.56, 15.53, 15.91, 16.03, 16.43, 16.64 (Me), 28.84 (CH$_2$), 126.35, 129.45, 131.49, 131.61, 132.61, 132.22, 134.90, 137.18, 140.37, 150.48 (ring Cs).
HRMS (EI): Calc: 212.1565 Found: 212.1567.

(ii) Synthesis of EBI*Na$_2$

Na (0.17 g, 7.56×10$^{-3}$ mol) was stirred in THF with naphthalene (1.04 g, 8.11×10$^{-3}$ mol) for 15 hours, resulting in a deep green solution of C$_{10}$H$_8$Na. After cooling to −78° C., a solution in THF of 2,3,4,5,6,7-hexamethyl-1-methylene-indene (1.50 g, 7.06×10$^{-3}$ mol) was added. The mixture was stirred for 2 hours at −78° C. and then allowed to warm to room temperature. Removal of the solvent under vacuum afforded a light brown solid, which was washed with Et$_2$O and filtered to give a light brown pyrophoric powder. Yield: 1.26 g, 76%.

Characterising Data:
$^1$H NMR (d$_5$-pyridine) δ (ppm): 2.49 (s, 12H, Me), 2.55, 2.71, 2.72, 3.13 (all s, 6H, Me), 3.94 (s, 4H, C$_2$H$_4$).

$^{13}$C NMR (d$_5$-pyridine) δ (ppm): 13.59, 16.41, 17.33, 17.46, 18.60, 19.05 (Me), 35.06 (C$_2$H$_4$), 97.01, 104.27, 117.68, 118.07, 123.12, 123.17, 123.77, 125.20, 125.79 (ring Cs).

The reaction mechanism for the above reaction is shown in Scheme 2 below.

Scheme 2: reaction mechanism

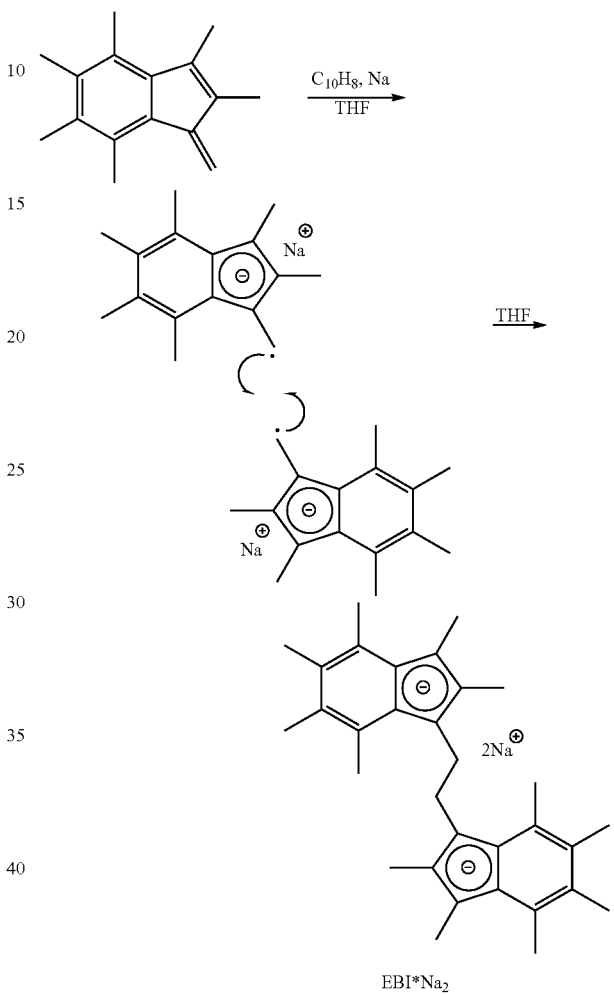

Example 1

Preparation of ethylene-bis-hexamethylindenyl zirconium chloride (EBI*ZrCl$_2$)

Scheme 3: synthesis of rac and meso-EBI*ZrCl$_2$

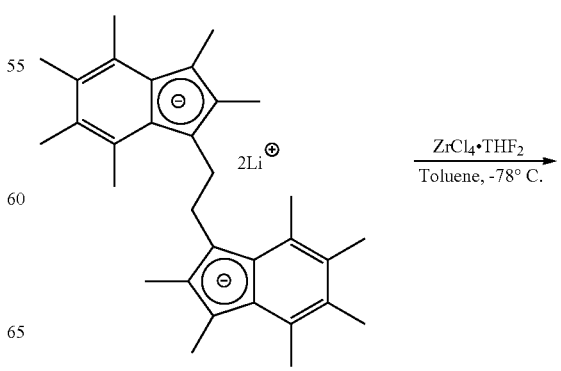

-continued

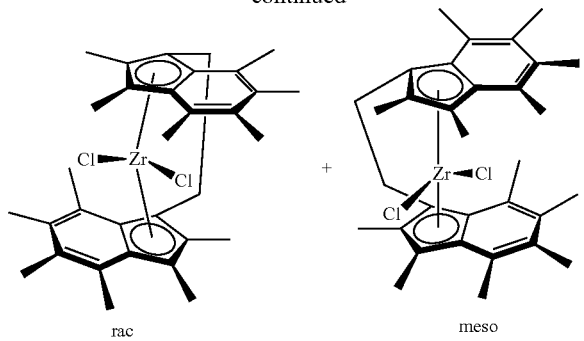

rac                    meso

EBI*Li$_2$.THF$_{0.38}$ (0.350 g, 7.51×10$^{-4}$ mol) was slurried in toluene and cooled to −78° C. To this orange-red slurry was added a white slurry of ZrCl$_4$.THF$_2$ (0.284 g, 7.51×10$^{-4}$ mol) in toluene. No immediate change was observed and the reaction mixture was allowed to warm to room temperature with stirring. After stirring for a further 15 hours, the red-brown reaction mixture was filtered affording a red-orange solution. The residues were extracted with CH$_2$Cl$_2$ and the extracts combined. Removal of the solvent under vacuum gave a red-orange solid, which was washed with −78° C. hexane. The resultant residue was extracted with room temperature hexane to give a red-orange solid and yellow-orange solution. NMR analysis of this solid showed it to be an approximately 1:0.8 rac/meso mix. The solvent was removed under vacuum from the yellow-orange solution to give an orange solid; NMR analysis of this solid indicated it to be mainly composed of meso-EBI*ZrCl$_2$ with a tiny proportion of impurities including the rac-isomer.

The rac/meso mix was extracted and filtered with CH$_2$Cl$_2$ to afford a red solution which was layered with hexane. The yellow supernatant was decanted via cannula leaving an orange solid, shown by NMR analysis to be pure rac-EBI*ZrCl$_2$. The supernatant was reduced under vacuum to an orange solid; a more meso enriched mixture of isomers; and washed with 60° C. hexane, leaving pure rac isomer. The orange-yellow solution was again reduced to an isomeric solid mix, extracted with 60° C. hexane and cooled to −80° C., depositing a final crop of rac-EBI*ZrCl$_2$. Crystals of rac-EBI*ZrCl$_2$ suitable for X-ray diffraction were grown as pale orange plates by layering a CD$_2$Cl$_2$ solution of the sample with Et$_2$O.

The predominantly meso extracts were further extracted with 60° C. hexane and filtered, reduced to a minimum volume and cooled slowly to −35° C. Orange needles of pure meso-EBI*ZrCl$_2$ suitable for X-ray diffraction were collected and washed with −78° C. hexane.

Yield: 0.060 g, 0.028 g, total 20%.

Characterising Data:

HRMS (EI): Calc: 584.1554 Found: 584.1567.

rac-EBI*ZrCl$_2$:

$^1$H NMR (C$_6$D$_6$) δ (ppm): 1.78, 2.11, 2.22, 2.43, 2.46, 2.56 (all s, 6H, Me), 3.22-3.40, 3.70-3.88 (m, 4H, C$_2$H$_4$).

$^1$H NMR (CDCl$_3$) δ (ppm): 1.84, 2.23, 2.29, 2.33, 2.40, 2.79 (all s, 6H, Me), 3.65-3.81, 4.02-4.18 (m, 4H, C$_2$H$_4$).

$^1$H NMR (CD$_2$Cl$_2$) δ (ppm): 1.84, 2.24, 2.29, 2.31, 2.37, 2.80 (all s, 6H, Me), 4.03-4.22, 3.63-3.82 (m, 4H, C$_2$H$_4$).

$^{13}$C NMR (CD$_2$Cl$_2$) δ (ppm): 11.96, 15.91, 16.58, 16.91, 17.71, 17.95 (Me), 32.94 (C$_2$H$_4$), 115.97, 118.84, 123.56, 125.21, 126.40, 128.84, 129.46, 130.65, 134.59 (ring Cs).

Anal. Calc for C$_{32}$H$_{40}$ZrCl$_2$: C, 65.50; H, 6.87. Found: C, 65.44; H, 6.79.

meso-EBI*ZrCl$_2$:

$^1$H NMR (C$_6$D$_6$) δ (ppm): 1.85, 1.99, 2.01, 2.39, 2.51, 2.52 (all s, 6H, Me), 3.20-3.34 3.74-3.88 (m, 4H, C$_2$H$_4$).

$^1$H NMR (CDCl$_3$) δ (ppm): 2.12, 2.13, 2.16, 2.32, 2.45, 2.60 (all s, 6H, Me), 3.63-3.80, 4.07-4.24 (m, 4H, C$_2$H$_4$).

$^1$H NMR (CD$_2$Cl$_2$) δ (ppm): 2.13 (s, 12H, Me), 2.17, 2.29, 2.43, 2.61 (all s, 6H, Me), 3.64-3.82, 4.08-4.26 (m, 4H, C$_2$H$_4$).

$^{13}$C NMR (C$_6$D$_6$) δ (ppm): 13.27, 15.71, 16.51, 16.87, 17.59, 17.71 (Me), 31.39 (C$_2$H$_4$), 106.72, 113.97, 121.50, 126.97, 127.29, 129.03, 130.68, 132.98, 134.05 (ring Cs).

$^{13}$C NMR (CDCl$_3$) δ (ppm): 13.45, 15.41, 16.45, 16.82, 17.40, 17.43 (Me), 31.34 (C$_2$H$_4$), 104.09, 114.17, 121.62, 126.25, 126.75, 129.52, 130.21, 133.03, 134.29 (ring Cs).

Structural Analysis of rac-EBI*ZrCl$_2$

As stated above, single crystals of rac-EBI*ZrCl$_2$ suitable for X-ray diffraction were grown as pale orange plates by the layering of a sample in CD$_2$Cl$_2$ with Et$_2$O. The compound crystallises in the monoclinic space group C2/c, and four alternate views are shown in FIG. 1. The compound is located on a crystallographic twofold axis of rotation, hence both indenyl rings are equivalent and relevant bond lengths and angles are given in Table 1 below.

TABLE 1

Selected bond lengths and angles for rac-EBI*ZrCl$_2$. Estimated standard deviations (ESDs) are given in parentheses

| Lengths (Å) | | | |
|---|---|---|---|
| Zr(1)—C(3) | 2.479(3) | C(4)—C(14) | 1.439(4) |
| Zr(1)—C(4) | 2.558(3) | C(5)—C(10) | 1.430(4) |
| Zr(1)—C(5) | 2.612(3) | C(10)—C(12) | 1.385(4) |
| Zr(1)—C(6) | 2.582(3) | C(12)—C(13) | 1.432(4) |
| Zr(1)—C(7) | 2.520(3) | C(13)—C(14) | 1.382(4) |
| C(3)—C(4) | 1.448(4) | C(3)—C(18) | 1.504(4) |
| C(4)—C(5) | 1.443(4) | C(18)—C(18)* | 1.546(6) |
| C(5)—C(6) | 1.437(4) | Avg. C$_5$—Me | 1.505 |
| C(6)—C(7) | 1.414(4) | Avg. C$_6$—Me | 1.514 |
| C(7)—C(3) | 1.430(4) | Zr(1)—Cp$_{cent}$ | 2.240 |
| | | Zr(1)—Cl(2) | 2.4358(7) |
| | | Δ$_{M-C}$ | 0.054 |
| Angles (°) | | | |
| C$_6$—C$_5$ planes | 2.6 | δ | 129.4 |
| Cl(2)—Zr—Cl(2)* | 96.24(4) | Hinge Angle | 2.7 |
| α α' | 57.2 55.6 | Rotation Angle | 124.4 |
| β β' | −1.1 0.3 | | |

Structural Analysis of meso-EBI*ZrCl$_2$

As stated above, X-ray quality crystals of meso-EBI*ZrCl$_2$ were obtained as orange needles by the slow cooling of a concentrated hexane solution to −35° C. The compound crystallises in the triclinic space group P$\bar{1}$, with one EBI* moiety and one toluene molecule per asymmetric unit. Alternate views are shown in FIG. 2, and relevant bond distances and angles are given in Table 2.

TABLE 2

Selected bond lengths and angles for meso-EBI*ZrCl$_2$. Estimated standard deviations (ESDs) are given in parentheses

| Lengths (Å) | | | |
|---|---|---|---|
| Zr(1)—C(13) | 2.470(5) | Zr(1)—C(4) | 2.627(5) |
| Zr(1)—C(14) | 2.557(5) | Zr(1)—C(5) | 2.596(5) |
| Zr(1)—C(15) | 2.574(5) | Zr(1)—C(6) | 2.487(5) |
| Zr(1)—C(16) | 2.597(5) | Zr(1)—C(7) | 2.504(5) |
| Zr(1)—C(17) | 2.556(5) | Zr(1)—C(8) | 2.570(5) |
| C(13)—C(14) | 1.442(8) | C(4)—C(5) | 1.441(7) |
| C(14)—C(15) | 1.438(8) | C(5)—C(6) | 1.448(8) |

TABLE 2-continued

Selected bond lengths and angles for meso-EBI*ZrCl$_2$. Estimated standard deviations (ESDs) are given in parentheses

| | | | |
|---|---|---|---|
| C(15)—C(16) | 1.436(8) | C(6)—C(7) | 1.422(8) |
| C(16)—C(17) | 1.402(8) | C(7)—C(8) | 1.412(8) |
| C(17)—C(13) | 1.417(8) | C(8)—C(4) | 1.441(7) |
| C(15)—C(20) | 1.435(8) | C(5)—C(28) | 1.429(8) |
| C(20)—C(22) | 1.384(9) | C(28)—C(29) | 1.373(9) |
| C(22)—C(23) | 1.422(10) | C(29)—C(31) | 1.422(9) |
| C(23)—C(24) | 1.369(9) | C(31)—C(32) | 1.379(8) |
| C(24)—C(14) | 1.424(8) | C(32)—C(4) | 1.434(8) |
| C(13)—C(12) | 1.521(8) | C(6)—C(11) | 1.501(8) |
| C(12)—C(11) | 1.539(9) | | |
| Avg. C$_5$—Me | 1.512 | Avg. C$_5$—Me | 1.508 |
| Avg. C$_6$—Me | 1.513 | Avg. C$_6$—Me | 1.513 |
| Zr(1)—Cp$_{cent}$ | 2.244 | Hf(1)—Cp$_{cent}$ | 2.248 |
| Zr(1)—Cl(2) | 2.4276(13) | Zr(1)—Cl(3) | 2.4571(14) |
| $\Delta_{M-C}$ | 0.033 | $\Delta_{M-C}$ | 0.082 |
| Angles (°) | | | |
| C$_6$—C$_5$ planes | 6.4 | C$_6$—C$_5$ planes | 3.9 |
| Cl(2)—Zr—Cl(3) | 97.41(5) | | |
| α α' | 56.9 54.4 | | |
| β β' | 1.3 2.9 | β β' | 1.0 1.9 |
| δ | 128.73 | | |
| Hinge Angle | 6.0 | Hinge Angle | 3.3 |
| Rotation Angle | 46.8 | | |

Example 2

Preparation of ethylene-bis-hexamethylindenyl hafnium chloride (EBI*HfCl$_2$)

Scheme 4: Synthesis of rac and meso-EBI*HfCl$_2$

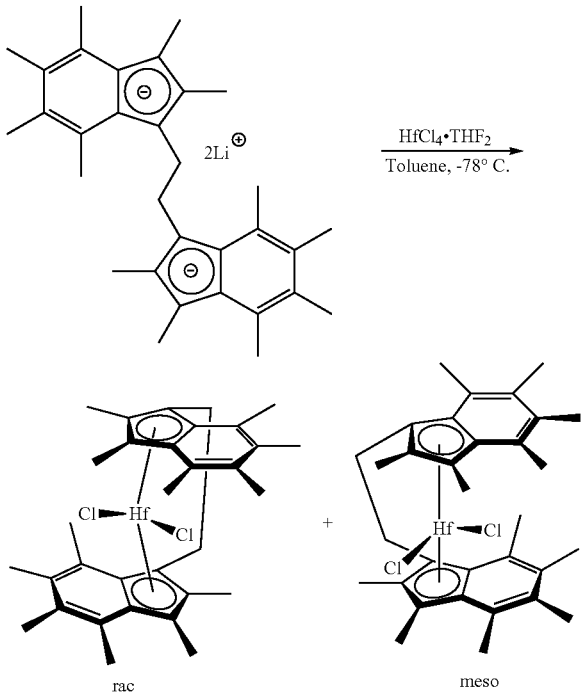

rac           meso

To an orange-red slurry of EBI*Li$_2$.THF$_{0.38}$ (0.350 g, 7.51×10$^{-4}$ mol) in toluene at −78° C. was added a white slurry of HfCl$_4$.THF$_2$ (0.349 g, 7.51×10$^{-4}$ mol) in toluene. The reaction mixture was allowed to warm to room temperature with stirring, with no observed change. After stirring for 15 hours, an aliquot was taken and NMR analysis showed a 1.7:1 mix of meso/rac isomers. The yellow-brown reaction mixture was filtered, and the remaining solid extracted with toluene and combined to give an orange-brown solution. Removal of the solvent under vacuum afforded a yellow-orange solid which was extracted with 60° C. hexane, giving a bright yellow solution and buff powder, shown by NMR analysis to be a 1:1 mix of rac/meso isomers. Removal of the solvent under vacuum from the bright yellow solution left a bright yellow solid, consisting by NMR analysis of predominantly meso-EBI*HfCl$_2$ with a small amount of the rac-isomer, and was purified to the pure meso form by extraction with room temperature hexane and filtration.

The buff rac/meso mix was extracted with 60° C. hexane and filtered giving a yellow solution, removal of the solvent under vacuum from which gave a solid consisting of mainly the meso-isomer with a small impurity including the rac form. Another extraction of this solid with 60° C. hexane afforded a yellow solution plus yellow solid. This yellow solid was dissolved in CH$_2$Cl$_2$, reduced to a minimum volume and layered with hexane. A light yellow solid precipitated and removal of the supernatant via cannula left pure rac-EBI*HfCl$_2$. The second yellow hexane extraction was reduced to a minimum volume and cooled to −35° C., whereupon a bright yellow solid crop of meso-EBI*HfCl$_2$ was collected and washed with −78° C. hexane.

Single crystals of the meso form suitable for analysis by X-ray diffraction were grown as pale yellow plates by the cooling of a saturated isomerically pure hexane solution of meso-EBI*HfCl$_2$ to −35° C. X-ray diffraction quality crystals of the rac-isomer were obtained as pale yellow needles by the slow evaporation of an NMR pure C$_6$D$_6$ solution of rac-EBI*HfCl$_2$.

Yield: 0.095 g, 0.057 g, total 30%.

Characterising Data:

MS (EI): Calc: 674.1957 Found: 674.1969.

rac-EBI*HfCl$_2$:

$^1$H NMR (C$_6$D$_6$) δ (ppm): 1.82, 2.12, 2.25, 2.46, 2.48, 2.55 (all s, 6H, Me), 3.43-3.52, 3.66-3.75 (m, 4H, C$_2$H$_4$).

$^1$H NMR (CDCl$_3$) δ (ppm): 1.88, 2.24, 2.31 (all s, 6H, Me), 2.38 (s, 12H, Me), 2.77 (s, 6H, Me), 3.83-3.94, 3.95-4.06 (m, 4H, C$_2$H$_4$).

$^1$H NMR (CD$_2$Cl$_2$) δ (ppm): 1.89, 2.26, 2.32, 2.34, 2.36, 2.79 (all s, 6H, Me), 3.85-3.94, 3.98-4.07 (m, 4H, C$_2$H$_4$).

$^{13}$C NMR (CD$_2$Cl$_2$) δ (ppm): 11.49, 15.72, 16.17, 16.49, 16.82, 17.68 (Me), 32.18 (C$_2$H$_4$), ring Cs not visible.

Anal. Calc for C$_{32}$H$_{40}$HfCl$_2$: C, 57.02; H, 5.98. Found: C, 57.08; H, 6.06.

meso-EBI*HfCl$_2$:

$^1$H NMR (C$_6$D$_6$) δ (ppm): 1.90, 2.01, 2.03, 2.39, 2.49, 2.57 (all s, 6H, Me), 3.23-3.40, 3.78-3.95 (m, 4H, C$_2$H$_4$).

$^1$H NMR (CDCl$_3$) δ (ppm): 2.13, 2.15, 2.22, 2.32, 2.51, 2.57 (all s, 6H, Me), 3.68-3.84, 4.11-4.27 (m, 4H, C$_2$H$_4$).

$^{13}$C NMR (C$_6$D$_6$) δ (ppm): 13.19, 15.47, 16.43, 16.79, 17.57, 17.69 (Me), 30.70 (C$_2$H$_4$), 110.79, 119.11, 125.30, 126.17, 126.33, 127.41, 130.46, 132.74, 133.76 (ring Cs).

$^{13}$C NMR (CDCl$_3$) δ (ppm): 13.72, 15.17, 16.36, 16.71, 17.38, 17.41 (Me), 30.61 (C$_2$H$_4$), 110.91, 119.17, 124.88, 125.39, 126.47, 127.88, 129.97, 132.77, 133.96 (ring Cs).

Characterisation of EBI*HfCl$_2$

Both isomers of EBI*HfCl$_2$ were characterised by $^1$H and $^{13}$C NMR spectroscopy, MS, EA, single-crystal X-ray diffraction and electrochemical studies. The $^1$H NMR spectral data of rac and meso-EBI*HfCl$_2$ were similar to those observed with rac and meso-EBI*ZrCl$_2$, in a number of different solvents. This implies the Zr and Hf species also have similar structures in solution.

Structural Analysis of rac-EBI*HfCl$_2$

As stated above, single crystals of rac-EBI*HfCl$_2$ suitable for X-ray diffraction were grown as pale yellow needles by the slow evaporation of a C$_6$D$_6$ solution. The molecule crystallises in the monoclinic space group C2/c, with 0.5 EBI* moieties per asymmetric unit. Four alternate views are shown in FIG. 3 and relevant bond distances and angles are given in Table 3.

As shown in Table 3 below, many structural parameters of rac-EBI*HfCl$_2$ are very similar to those of the Zr analogue given in Table 1. The EBI* moiety bonds to the metal centre in a similar bis-η$^5$ manner, the replacement of the second row transition metal element with its smaller third row equivalent resulting in an decrease in the M-Cp$_{cent}$ distance of 0.018 Å. FIG. 3 clearly shows the large tilt angle α, and the unusual negative value of β, as in rac-EBI*ZrCl$_2$

TABLE 3

Selected bond lengths and angles for rac-EBI*HfCl$_2$. Estimated standard deviations (ESDs) are given in parentheses

| Lengths (Å) | | | |
|---|---|---|---|
| Hf(1)—C(3) | 2.498(3) | C(5)—C(12) | 1.440(4) |
| Hf(1)—C(4) | 2.462(3) | C(6)—C(9) | 1.433(4) |
| Hf(1)—C(5) | 2.541(3) | C(9)—C(10) | 1.379(4) |
| Hf(1)—C(6) | 2.598(3) | C(10)—C(11) | 1.441(4) |
| Hf(1)—C(7) | 2.571(3) | C(11)—C(12) | 1.378(4) |
| C(3)—C(4) | 1.426(4) | C(4)—C(41) | 1.507(4) |
| C(4)—C(5) | 1.446(4) | C(41)—C(41)* | 1.554(6) |
| C(5)—C(6) | 1.448(4) | Avg. C$_5$—Me | 1.508 |
| C(6)—C(7) | 1.433(4) | Avg. C$_6$—Me | 1.511 |
| C(7)—C(3) | 1.417(4) | Hf(1)—Cp$_{cent}$ | 2.222 |
| | | Hf(1)—Cl(2) | 2.4118(7) |
| | | Δ$_{M-C}$ | 0.053 |
| Angles (°) | | | |
| C$_6$—C$_5$ planes | 2.5 | δ | 129.9 |
| Cl(2)—Hf—Cl(2)* | 95.43(4) | Hinge Angle | 2.0 |
| α α' | 57.0 55.9 | Rotation Angle | 125.2 |
| β β' | −1.5 0.9 | | |

Structural Analysis of meso-EBI*HfCl$_2$

As stated above, the slow cooling to −35° C. of a concentrated toluene solution of meso-EBI*HfCl$_2$ afforded pale yellow plates suitable for study by X-ray diffraction. The compound crystallises in the monoclinic space group P2$_1$/n, with one EBI* moiety in the asymmetric unit. For alternate views are shown in FIG. 4, and selected bond distances and angles are given in Table 4.

TABLE 4

Selected bond lengths and angles for meso-EBI*HfCl$_2$. Estimated standard deviations (ESDs) are given in parentheses

| Lengths (Å) | | | |
|---|---|---|---|
| Hf(1)—C(7) | 2.562(6) | Hf(1)—C(22) | 2.453(5) |
| Hf(1)—C(8) | 2.459(5) | Hf(1)—C(24) | 2.534(5) |
| Hf(1)—C(9) | 2.478(6) | Hf(1)—C(30) | 2.577(5) |
| Hf(1)—C(11) | 2.553(5) | Hf(1)—C(31) | 2.593(6) |
| Hf(1)—C(12) | 2.622(5) | Hf(1)—C(32) | 2.527(5) |
| C(7)—C(8) | 1.436(8) | C(22)—C(24) | 1.438(8) |
| C(8)—C(9) | 1.402(8) | C(24)—C(30) | 1.446(7) |
| C(9)—C(11) | 1.428(8) | C(30)—C(31) | 1.437(8) |
| C(11)—C(12) | 1.432(8) | C(31)—C(32) | 1.415(8) |
| C(12)—C(7) | 1.445(8) | C(32)—C(22) | 1.428(8) |
| C(12)—C(13) | 1.421(8) | C(24)—C(25) | 1.429(8) |
| C(13)—C(15) | 1.371(9) | C(25)—C(27) | 1.378(8) |
| C(15)—C(16) | 1.439(10) | C(27)—C(28) | 1.423(9) |
| C(16)—C(17) | 1.374(9) | C(28)—C(29) | 1.389(9) |
| C(17)—C(7) | 1.450(8) | C(29)—C(30) | 1.418(8) |
| C(8)—C(20) | 1.511(8) | C(22)—C(21) | 1.519(7) |
| C(20)—C(21) | 1.551(9) | — | |
| Avg. C$_5$—Me | 1.511 | Avg. C$_5$—Me | 1.513 |
| Avg. C$_6$—Me | 1.516 | Avg. C$_6$—Me | 1.515 |
| Hf(1)—Cp$_{cent}$ | 2.225 | Hf(1)—Cp$_{cent}$ | 2.226 |
| Hf(1)—Cl(2) | 2.4215(13) | Hf(1)—Cl(6) | 2.3953(13) |
| Δ$_{M-C}$ | 0.086 | Δ$_{M-C}$ | 0.030 |
| Angles (°) | | | |
| C$_6$—C$_5$ planes | 1.5 | C$_6$—C$_5$ planes | 2.3 |
| Cl(2)—Hf—Cl(6) | 96.02(5) | — | |
| α α' | 56.9 55.1 | — | |
| β β' | 0.2 0.5 | β β' | 0.9 2.1 |
| δ | 129.9 | — | |
| Hinge Angle | 2.6 | Hinge Angle | 4.2 |
| Rotation Angle | 45.0 | — | |

Example 3

Preparation of ethylene-bis-hexamethylindenyl titanium chloride (EBI*TiCl$_2$)

Scheme 4: Synthesis of rac-EBI*TiCl$_2$

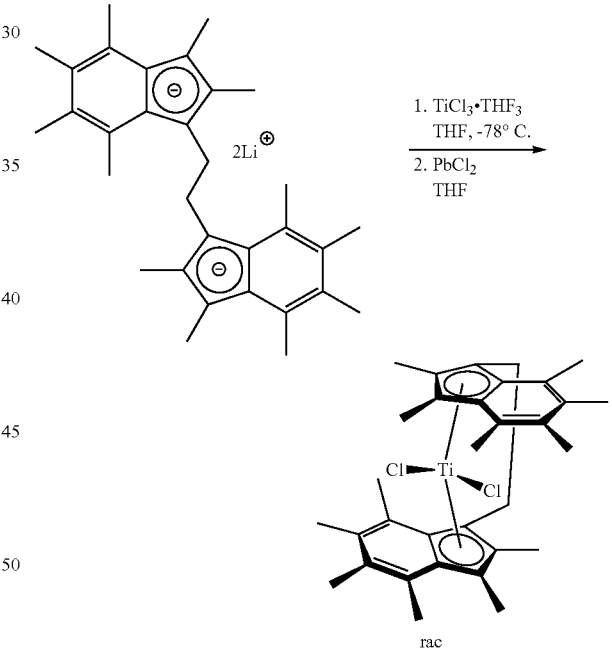

rac

EBI*Li$_2$.THF$_{0.38}$ (0.075 g, 1.61×10$^{-4}$ mol) was slurried in toluene and cooled to −78° C. To this buff slurry was added a bright blue solution of TiCl$_3$.THF$_3$ (0.060 g, 1.61×10$^{-4}$ mol) in THF. The reaction mixture was observed to darken, and on warming to room temperature a red-brown solution was obtained. The reaction mixture was stirred for a further 15 hours at room temperature, then transferred via cannula onto a slurry of PbCl$_2$ (0.030 g, 1.05×10$^{-4}$ mol) in THF. The reaction mixture changed to a yellow-green colour, and a dark grey solid was seen on the bottom of the Schlenk, presumed to be Pb. The reaction mixture was stirred for another 15 hours and left to settle, affording a green-yellow solution with dark grey solid and a dark grey metallic rim at the solvent edge. Filtration and removal of the solvent under vacuum left a dark green solid, shown by NMR analysis to contain peaks consistent with EBI*TiCl$_2$ together with EBI*H$_2$ and fulvene peaks. The residue was washed with hexane, dissolved in a minimum volume of toluene and the green solution cooled to −78° C. A solid precipitated and was collected by filtration, washed with −78° C. toluene, NMR analysis showing it to be consistent with the formula of the desired product EBI*TiCl$_2$. Yield: 0.009 g, 10%.

Characterising Data:
rac-EBI*TiCl$_2$

MS (EI): Calc: 542.1987 Found: 542.1994.

$^1$H NMR (C$_6$D$_6$) δ (ppm): 1.70, 2.11, 2.23, 2.46, 2.47, 2.59 (all s, 6H, Me), 3.25-3.42, 3.86-4.03 (m, 4H, C$_2$H$_4$).

$^1$H NMR (CDCl$_3$) δ (ppm): 1.74, 2.25, 2.32, 2.35, 2.40, 2.84 (all s, 6H, Me), 3.74-3.90, 4.26-4.42 (m, 4H, C$_2$H$_4$).

$^1$H NMR (d$_8$-toluene) δ (ppm): 1.68, 2.11, 2.21, 2.40, 2.42, 2.60 (all s, 6H, Me), sample too weak to assign C$_2$H$_4$ multiplet accurately.

Example 4

Preparation of EBI*ZrMe$_2$ rac-EBI*ZrCl$_2$ was suspended in Et$_2$O and cooled to −78° C. To this orange suspension was added an excess of 1.56M MeLi.LiBr in Et$_2$O, and the reaction mixture allowed to warm to room temperature. The initial orange suspension became a yellow solution and was stirred for a further 2 hours. Removal of the solvent under vacuum, extraction with hexane and removal of the volatiles afforded a light orange-yellow solid, shown by NMR analysis to be meso-EBI*ZrMe$_2$. The use of low halide MeLi in Et$_2$O with rac-EBI*ZrCl$_2$ was found to yield rac-EBI*ZrMe$_2$. A similar procedure was followed with meso-EBI*ZrCl$_2$ and 1.56M MeLi.LiBr in Et$_2$O, affording meso-EBI*ZrMe$_2$.

Characterising Data:
rac-EBI*ZrMe$_2$:

$^1$H NMR (C$_6$D$_6$) δ (ppm): −0.99 (s, 6H, Zr-Me), 1.69, 2.12, 2.22, 2.41, 2.49, 2.51 (all s, 6H, Me), 3.12-3.29, 3.41-3.58 (m, 4H, C$_2$H$_4$).

meso-EBI*ZrMe$_2$:

$^1$H NMR (C$_6$D$_6$) δ (ppm): −2.33, −0.20 (both s, 3H, Zr-Me), 1.77, 2.04, 2.07, 2.41, 2.42, 2.48 (all s, 6H, Me), 2.95-3.12, 3.53-3.70 (m, 4H, C$_2$H$_4$).

$^1$H NMR (CDCl$_3$) δ (ppm): −2.88, −0.62 (both s, 3H, Zr-Me), 2.03, 2.11, 2.14, 2.38, 2.39, 2.48 (all s, 6H, Me), 3.23-3.38, 3.68-3.83 (m, 4H, C$_2$H$_4$).

Example 5

Preparation of EBI*Zr(CH$_2$R)$_2$ (where R is phenyl, tertiary butyl or trimethylsilane)

To an NMR tube containing a suspension of rac-EBI*ZrCl$_2$ in C$_6$D$_6$ was added an excess of either KCH$_2$Ph, LiCH$_2$SiMe$_3$ or LiCH$_2$$^t$Bu. The tube was sonicated for 10 minutes and the NMR spectrum acquired. In the cases with KCH$_2$Ph and LiCH$_2$SiMe$_3$, initial NMR analysis indicated the reaction was instantaneous, forming meso-EBI*(CH$_2$Ph)$_2$ and rac-EBI*Zr(CH$_2$SiMe$_3$)$_2$ respectively. The reaction of rac-EBI*ZrCl$_2$ with LiCH$_2$$^t$Bu initially showed some starting materials to remain, however after being left for 15 hours NMR analysis indicated complete conversion to rac-EBI*Zr(CH$_2$$^t$Bu)$_2$.

Characterising Data:
meso-EBI*Zr(CH$_2$$^t$Bu)$_2$:

$^1$H NMR (C$_6$D$_6$) δ (ppm): −2.19, 0.43 (both s, 2H, Zr—CH$_2$$^t$Bu), 0.59, 1.40 (both s, 9H, CH$_2$CMe$_3$), 1.96, 2.13, 2.15, 2.47, 2.52, 2.60 (all s, 6H, Me), 3.00-3.11, 3.60-3.71 (m, 4H, C$_2$H$_4$).

rac-EBI*Zr(CH$_2$SiMe$_3$)$_2$:

$^1$H NMR (C$_6$D$_6$) δ (ppm): −1.73, −0.21 (both d, 2H, J=10.50 Hz, Zr—CH$_2$TMS), 0.09 (s, 18H, CH$_2$SiMe$_3$), 1.80, 2.12, 2.24, 2.46, 2.53, 2.57 (all s, 6H, Me), 3.12-3.31, 3.39-3.58 (m, 4H, C$_2$H$_4$).

meso-EBI*Zr(CH$_2$Ph)$_2$:

$^1$H NMR (C$_6$D$_6$) δ (ppm): −0.72, 1.82 (both s, 2H, Zr—CH$_2$Ph), 1.84, 2.00 (both s, 6H, Me), 2.03 (s, 12H, Me), 2.40, 2.49 (both s, 6H, Me), 2.98-3.16, 3.58-3.76 (m, 4H, C$_2$H$_4$), 6.39, 6.57 (both d, 2H, J=6.6 Hz, CH$_2$C$_6$H$_2$$^{ortho}$H$_2$$^{meta}$H$^{para}$) 6.80, 6.94 (both t, 1H, CH$_2$C$_6$H$_2$$^{ortho}$H$_2$$^{meta}$H$^{para}$), 7.05, 7.13, (both t, 2H, CH$_2$C$_6$H$_2$$^{ortho}$H$_2$$^{meta}$H$^{para}$).

Example 6

Preparation of EBI*HfMe$_2$ rac-EBI*HfCl$_2$ was dissolved in Et$_2$O, cooled to −78° C. and an excess of 1.56M MeLi.LiBr in Et$_2$O added, the mixture becoming lighter in colour. After stirring for 2 hours, the solvent was removed under vacuum. Extraction with hexane afforded a light yellow solution, and removal of the solvent under vacuum a light yellow solid shown by NMR analysis to be rac-EBI*HfMe$_2$.

meso-EBI*HfCl$_2$ was treated in the same way, the hexane extracts being almost colourless and removal of the solvent under vacuum affording an off-white solid. This was shown by NMR analysis to be meso-EBI*HfMe$_2$.

Characterising Data:
rac-EBI*HfMe$_2$:

$^1$H NMR (C$_6$D$_6$) δ (ppm): −1.18 (s, 6H, Hf-Me), 1.70, 2.12, 2.23, 2.41, 2.49, 2.53 (all s, 6H, Me), 3.28-3.36, 3.42-3.50 (m, 4H, C$_2$H$_4$).

meso-EBI*HfMe$_2$:

$^1$H NMR (C$_6$D$_6$) δ (ppm): −2.59, −0.39 (both s, 3H, Hf-Me), 1.83, 2.04, 2.07, 2.41, 2.42, 2.46 (all s, 6H, Me), 3.03-3.20, 3.58-3.75 (m, 4H, C$_2$H$_4$).

$^{13}$C NMR (C$_6$D$_6$) δ (ppm): 13.12, 14.44, 16.35, 16.68, 17.47, 17.55 (Me), 29.88 (C$_2$H$_4$), 92.85, 106.04, 110.34, 123.92 (ring Cs), other ring Cs not visible.

Example 7

Preparation of EBI*Hf(CH$_2$R)$_2$ (where R is phenyl, tertiary butyl or trimethylsilane)

To an NMR tube containing an orange solution of rac-EBI*HfCl$_2$ in C$_6$D$_6$ was added an excess of either KCH$_2$Ph, LiCH$_2$SiMe$_3$ or LiCH$_2$$^t$Bu. The tube was sonicated for 10 minutes and the NMR spectrum obtained, showing complete conversion to rac-EBI*Hf(CH$_2$R)$_2$.

A bright yellow solution of meso-EBI*HfCl$_2$ in C$_6$D$_6$ was treated with an excess of either KCH$_2$Ph, LiCH$_2$SiMe$_3$ or LiCH$_2$$^t$Bu. After sonication for 10 minutes the NMR spectrum was obtained. Reaction with KCH$_2$Ph was instantaneous; those with LiCH$_2$SiMe$_3$ and LiCH$_2$$^t$Bu showed a mixture of meso-EBI*HfCl$_2$ and the desired product, and were left for a further 15 hours. NMR analysis of these samples showed complete conversion to meso-EBI*Hf(CH$_2$SiMe$_3$)$_2$ and meso-EBI*Hf(CH$_2$$^t$Bu)$_2$ respectively.

Characterising Data:

rac-EBI*Hf(CH$_2$$^t$Bu)$_2$:

$^1$H NMR (C$_6$D$_6$) δ (ppm): −1.36, −0.20 (both d, 2H, J=11.70 Hz, Hf—CH$_2$$^t$Bu), 1.00 (s, 18H, CH$_2$CMe$_3$), 1.93, 2.16, 2.25, 2.51, 2.55, 2.58 (all s, 6H, Me), sample too weak to assign C$_2$H$_4$ multiplet accurately.

meso-EBI*Hf(CH$_2$$^t$Bu)$_2$:

$^1$H NMR (C$_6$D$_6$) δ (ppm): −2.49, 0.08 (both s, 2H, Hf—CH$_2$$^t$Bu), 0.59, 1.40 (both s, 9H, CH$_2$CMe$_3$), 2.01, 2.13, 2.15, 2.49, 2.50, 2.67 (all s, 6H, Me), 3.06-3.22, 3.61-3.77 (m, 4H, C$_2$H$_4$).

rac-EBI*Hf(CH$_2$SiMe$_3$)$_2$:

$^1$H NMR (C$_6$D$_6$) δ (ppm): −1.95, −0.53 (both d, 2H, J=12.00 Hz, Hf—CH$_2$SiMe$_3$), 0.09 (s, 18H, CH$_2$SiMe$_3$), 1.81, 2.12, 2.25, 2.48, 2.53, 2.57 (all s, 6H, Me), sample too weak to assign C$_2$H$_4$ multiplet accurately.

meso-EBI*Hf(CH$_2$SiMe$_3$)$_2$:

$^1$H NMR (C$_6$D$_6$) δ (ppm): −3.32, −0.64 (both s, 2H, CH$_2$SiMe$_3$), 2.00, 2.07, 2.16, 2.44, 2.53, 2.59 (all s, 6H, Me), 3.00-3.27, 3.52-3.79 (m, 4H, C$_2$H$_4$), CH$_2$SiMe$_3$ peaks obscured by residual LiCH$_2$SiMe$_3$ resonances.

rac-EBI*Hf(CH$_2$Ph)$_2$:

$^1$H NMR (C$_6$D$_6$) δ (ppm): −0.36, 1.17 (both d, 2H, J=12.30 Hz, Hf—CH$_2$$^t$Bu), 1.67, 1.79, 2.15, 2.17, 2.31, 2.58 (all s, 6H, Me), 3.28-3.45, 3.48-3.65 (m, 4H, C$_2$H$_4$), 6.80-7.20 (m, 10H, CH$_2$Ph).

meso-EBI*Hf(CH$_2$Ph)$_2$:

$^1$H NMR (C$_6$D$_6$) δ(ppm): −0.92, 1.61 (both s, 2H, Hf—CH$_2$Ph), 1.94, 1.99, 2.01, 2.10, 2.39, 2.48 (all s, 6H, Me), 3.05-3.24, 3.62-3.81 (m, 4H, C$_2$H$_4$), 6.37, 6.72 (both d, 2H, J=7.2 Hz, CH$_2$C$_6$H$_2$$^{ortho}$H$_2$$^{meta}$H$^{para}$), 6.77, 6.96 (both t, 1H, CH$_2$C$_6$H$_2$$^{ortho}$H$_2$$^{meta}$H$^{para}$), 7.06, 7.17 (both t, 2H, CH$_2$C$_6$H$_2$$^{ortho}$H$_2$$^{meta}$H$_{para}$).

Example 8

Ethylene Polymerisations

The homogenous ethylene polymerisation activity of the catalysts prepared in examples 1 and 2 was evaluated. The catalysts were dissolved in toluene with half the modified methylaluminoxane (MMAO) activator added in this solution (5000 equivalents vs metal), and the other half added in the 5 L steel autoclaves. The polymerisation conditions and results are summarised in Table 5.

TABLE 5

Homogenous ethylene polymerisation conditions and results obtained with rac and meso-EBI*MCl$_2$ (M = Zr, Hf)

| Catalyst | Catalyst amount | MMAO | Run time | Polymer yield (g) | Productivity (g$_{PE}$/mol met/h) |
|---|---|---|---|---|---|
| rac-EBI*ZrCl$_2$ | 1.17 mg | 20 mmol | 15 min | 309 | 6.18 × 10$^8$ |
| meso-EBI*ZrCl$_2$ | 2 μmol Zr | 10000 eq/Zr | 30 min | 382 | 3.83 × 10$^8$ |
| rac-EBI*HfCl$_2$ | 1.35 mg | 20 mmol | 60 min | 25 | 1.25 × 10$^7$ |
| meso-EBI*HfCl$_2$ | 2 μmol Hf | 10000 eq/Hf |  | 67 | 3.35 × 10$^7$ |

Polymerisation conditions: 1.8 L isobutene, 70° C., P$_{C2}$ = 10 bar

As shown in Table 5, both rac and meso Zr compounds are very active in ethylene polymerisation, with catalytic activities obtained between 3×10$^8$ and 6×10$^8$ g$_{PE}$/mol Zr/h. The Hf analogues are less active, by a factor of approximately 49 for the rac compounds and approximately 11 for the meso forms. In the case of EBI*ZrCl$_2$, the rac isomer was approximately 1.6 times more active than the meso; this trend is reversed in EBI*HfCl$_2$, with the meso form being 2.7 times more active than the rac.

Comparative studies on the catalytic performance of other Group 4 metallocene compounds generally agree with the activity of Zr complexes being substantially higher than that of the corresponding Hf compounds under similar conditions.[2-4] Studies have been performed into the electronic and steric effects of the ligands, together with the polymerisation conditions, on the ethylene polymerisation activities of zirconocene catalysts.[5-8] The role of the aluminoxane co-catalyst has been examined, and for most homogenous metallocene catalysts a large excess of aluminoxane is required for the polymerisation to achieve its optimum productivity. The literature commonly reports Al/Zr ratios between 1000 to 50000, with activity generally increasing as the ratio increases, up to an optimal value. It is therefore important when comparing activity data to compare similar conditions and Al/Zr ratios where possible. MAO is the most commonly used aluminoxane, however it has been shown that MMAO/metallocene and MAO/metallocene systems have comparable polymerisation rates, hence values in this work can be readily compared with the literature.[9]

The effect of ligand substitution on the polymerisation activity has been rationalised on steric grounds, with unsubstituted zirconocene dichloride being more active than mixed sandwiches which are in turn more active than symmetrically substituted compounds, as shown in Table 6. The Me groups have a sterically hindering effect and decrease the flexibility towards the spatial requirements of the incoming monomer and the growing polymer chain.

TABLE 6

Ethylene polymerisation data, showing negative steric effect on catalytic activity of Cp based zirconocenes/MAO systems, together with activities of EBI* species in the same units

| Catalyst | Activity (kg$_{PE}$/g$_{Zr}$/h) | Al/Zr ratio | Ref. |
|---|---|---|---|
| Cp$_2$ZrCl$_2$ | 500 | 8000:1 | 18$^a$ |
| (CpMe$_4$H)CpZrCl$_2$ | 255 | 8000:1 | 18$^a$ |
| Cp*CpZrCl$_2$ | 170 | 8000:1 | 18$^a$ |
| (CpMe$_4$H)$_2$ZrCl$_2$ | 135 | 8000:1 | 18$^a$ |

TABLE 6-continued

Ethylene polymerisation data, showing negative steric effect on catalytic activity of Cp based zirconocenes/MAO systems, together with activities of EBI* species in the same units

| Catalyst | Activity ($kg_{PE}/g_{Zr}/h$) | Al/Zr ratio | Ref. |
|---|---|---|---|
| Cp*$_2$ZrCl$_2$ | 135 | 8000:1 | 18[a] |
| rac-EBI*ZrCl$_2$ | 6775 | 10000:1 | This invention[b] |
| meso-EBI*ZrCl$_2$ | 4187 | 10000:1 | This invention[b] |

[a]70° C., $P_{C2}$ = 5 bar;
[b]70° C., $P_{C2}$ = 10 bar

It can also be seen from Table 6 that, although the Al/Zr ratio is slightly higher for the EBI*ZrCl$_2$ samples, the activity is significantly greater than for all the Cp based Zr systems.

The data in Table 7 show that the unbridged Ind species Ind$_2$ZrCl$_2$ is approximately 3.7 times more active than Cp$_2$ZrCl$_2$. Furthermore, they indicate that the introduction of an ansa bridge in this Ind case reduces the activity of the resulting catalyst by almost 7 times to a value similar to that of Cp*$_2$ZrCl$_2$. These trends of decreasing activity with increasing steric substitution, and decreased activity of bridged compared with non-bridged species, has also been documented elsewhere in the literature.[10]

TABLE 7

Ethylene polymerisation data for a series of Cp and Ind based zirconocene catalysts

| Catalyst | Activity ($kg_{PE}/g_{Zr}/h$) | Al/Zr ratio | Ref. |
|---|---|---|---|
| Cp$_2$ZrCl$_2$ | 185 | 4000:1 | 18[a] |
| Cp*$_2$ZrCl$_2$ | 95 | 4000:1 | 18[a] |
| Ind$_2$ZrCl$_2$ | 686 | 5000:1 | 19[b] |
| rac-EBIZrCl$_2$ | 102 | 5000:1 | 19[b] |

[a]70° C., $P_{C2}$ = 5 bar;
[b]50° C., $P_{C2}$ = 2 bar

The data in Table 6 and Table 7 suggest that, even though information at equivalent Al/Zr ratios is not available, the EBI*ZrCl$_2$ catalysts are much more active than either the Cp based, unbridged Ind, or ansa Zr species given here. It appears that the EBI* ligand array counters the usual trends, being both ansa bridged and fully substituted yet also highly active.

As mentioned earlier, experimentally determined values of catalyst activity are highly dependent upon the precise reaction conditions, and often the kinetic profile or lifetime of the catalyst is not mentioned. However, to enable comparison of values in the literature, Gibson suggests converting activity figures to $g_{polymer}$/mmol metal/h/bar, and placing the catalyst on a scale of merit ranging from very low to very high. This scale is shown in Table 8, together with the converted values for the EBI*MCl$_2$ species tested.[12]

TABLE 8

Qualitative performance assignment for catalyst activities, together with converted values for EBI*MCl$_2$ species

| Performance | Activity ($g_{polymer}$/mmol met/h/bar) |
|---|---|
| Very low | less than 1 |
| Low | 1-10 |
| Moderate | 10-10$^2$ |

TABLE 8-continued

Qualitative performance assignment for catalyst activities, together with converted values for EBI*MCl$_2$ species

| | Activity ($g_{polymer}$/mmol met/h/bar) |
|---|---|
| High | 10$^2$-10$^3$ |
| Very high | greater than 10$^3$ |
| Catalyst | |
| rac-EBI*ZrCl$_2$ | 6.18 × 10$^4$ |
| meso-EBI*ZrCl$_2$ | 3.82 × 10$^4$ |
| rac-EBI*HfCl$_2$ | 1.25 × 10$^3$ |
| meso-EBI*HfCl$_2$ | 3.35 × 10$^3$ |

According to this scheme, each of the four EBI* catalysts tested have a very high activity rating in ethylene polymerisation. Under similar conditions (Al/Zr ratio 8300:1, 50° C., $P_{C2}$=2 bar) Ind$_2$ZrCl$_2$ and rac-EBIZrCl$_2$ have been reported to have activities of 1.40×10$^4$ and 1.30×10$^4$ $g_{PE}$/mmol Zr/h/bar respectively.[13] rac-EBI*ZrCl$_2$ surpasses this maximum activity by a factor of approximately five.

Samples of each polymer produced by EBI*MCl$_2$ catalysts were analysed by differential scanning calorimetry (DSC) in order to determine their melting points, and values obtained are shown in Table 9.

TABLE 9

Melting points of polyethylene samples prodcuced, measured by DSC

| Catalyst | Melting point of polyethylene produced (° C.) |
|---|---|
| rac-EBI*ZrCl$_2$ | 133.16 |
| meso-EBI*ZrCl$_2$ | 133.75 |
| rac-EBI*HfCl$_2$ | 134.59 |
| meso-EBI*HfCl$_2$ | 132.03 |

It can be seen that each of the four polyethylene samples analysed has a similar melting point. There is slightly more variation between the samples produced by the Hf catalysts than those produced by rac and meso-EBI*ZrCl$_2$. For comparison, the literature reports that polyethylene synthesised by meso-EBIZrCl$_2$ catalyst has a melting point determined by DSC of 123° C., compared with 135° C. for that of the rac analogue.[13,14] This reduction in melting point has been attributed to the introduction of short branches into the polyethylene chain and the formation of linear low-density polyethylene (LLDPE). However, a number of other polyethylene samples produced via ansa bridged substituted meso zirconocene catalysis show a melting point of approximately 133° C.[15] In general the melting points of EBI* catalysed polyethylene samples are comparable with those in the literature for non-branched, linear high-density polyethylene (HDPE).[16]

For comparison of their molecular weight distributions and a comparison of chain branching, each polyethylene sample has been further analysed by high temperature gel permeation chromatography (GPC); using both combined GPC-viscosity and conventional GPC approaches. The GPC system was calibrated in such a manner that combined GPC-viscosity could be used to give 'true' molecular weight data and conventional GPC could also be applied, results from the latter expressed as for linear polyethylene. GPC-viscosity was not used for the polypropylene oligomer since the viscosity detector response is effectively a function of molecular weight, hence the response to the propylene oligomer sample is too low for this technique to be sensible. These data are summarised in Table 10 as the calculated molecular weight averages (weight average molecular weight $M_w$, number average molecular weight $M_n$) and polydispersities ($M_w/M_n$).

TABLE 10

Molecular weight averages and polydispersities ($M_w/M_n$) for the four polyethylene samples produced, data obtained by high temperature GPC and combined GPC-viscosity, with duplicate runs performed for each sample

| Catalyst | Technique | $M_w$ | $M_n$ | $M_w/M_n$ |
|---|---|---|---|---|
| rac-EBI*ZrCl$_2$ | GPC | 215000 | 88800 | 2.4 |
| | | 215000 | 91200 | 2.4 |
| | GPC-viscosity | 217000 | 83200 | 2.6 |
| | | 216000 | 85000 | 2.5 |
| meso-EBI*ZrCl$_2$ | GPC | 203000 | 86100 | 2.4 |
| | | 203000 | 86400 | 2.4 |
| | GPC viscosity | 202000 | 80000 | 2.5 |
| | | 202000 | 79900 | 2.5 |
| rac-EBI*HfCl$_2$ | GPC | 228000 | 85600 | 2.7 |
| | | 227000 | 85100 | 2.7 |
| | GPC-viscosity | 228000 | 79800 | 2.9 |
| | | 225000 | 77700 | 2.9 |
| meso-EBI*HfCl$_2$ | GPC | 106000 | 33700 | 3.2 |
| | | 107000 | 34800 | 3.1 |
| | GPC viscosity | 103000 | 34200 | 3.0 |
| | | 103000 | 35200 | 2.9 |

It can clearly be seen from Table 10 that three of the four polyethylene samples have similar molecular weight distributions, however the sample produced by the meso-EBI*HfCl$_2$ catalyst is of considerable lower molecular weight (approximately half) and has the broadest distribution. Within the other three samples, there are small but clear differences; the polymer produced with rac-EBI*HfCl$_2$ as catalyst has the highest weight average molecular weight ($M_w$) and broadest distribution, while that from meso-EBI*ZrCl$_2$ has the lowest M. Although the $M_w$ and $M_n$ of the Zr catalysed samples are different, their polydispersities are identical. Within Hf catalysed samples, a similar effect is observed in polydispersities in the combined GPC-viscosity data. It appears that for both Zr and Hf catalysed polyethylene samples, the polymers with the highest $M_w$ are those of the rac rather than the meso catalysts. By reference to Table 9 it can be seen that there exists a correlation between the highest values of $M_w$, $M_n$ and melting point for the rac-EBI*HfCl$_2$ catalysed polymer, and the lowest values of $M_w$, $M_n$ and melting point for the resultant meso-EBI*HfCl$_2$ polyethylene.

It has been noted in the literature that molecular weight distributions of polymers obtained in ethylene polymerisation studies vary with the reaction conditions, making direct quantitative comparisons between previously published results difficult.[17,16] However, values of $M_w$ and polydispersity of EBI*MCl$_2$ catalysed polymers are similar to those found in the literature.[7,8,17] Some reported values of activity, $M_w$ and polydispersity for a number of metallocene catalysed polyethylene samples are given in Table 11.

TABLE 11

Comparison of activity, $M_w$ and polydispersity ($M_w/M_n$) for select Zr and Hf Ind catalysts in ethylene polymerisation

| Catalyst | Activity (kg$_{PE}$/mol met/h) | Al/Zr ratio | $M_w$ (× 10$^3$) | $M_w/M_n$ | Ref. |
|---|---|---|---|---|---|
| Ind$_2$ZrCl$_2$ | 62500 | 5000:1 | 490 | 2.3 | 19[a] |
| Ind$_2$HfCl$_2$ | 7812 | 5000:1 | 959 | 2.6 | 19[a] |

TABLE 11-continued

Comparison of activity, $M_w$ and polydispersity ($M_w/M_n$) for select Zr and Hf Ind catalysts in ethylene polymerisation

| Catalyst | Activity (kg$_{PE}$/mol met/h) | Al/Zr ratio | $M_w$ (× 10$^3$) | $M_w/M_n$ | Ref. |
|---|---|---|---|---|---|
| rac-EBIZrCl$_2$ | 9377 | 5000:1 | 240 | 3.2 | 19[a] |
| rac-EBIHfCl$_2$ | 2101 | 5000:1 | 387 | 4.4 | 19[a] |
| rac-EBIOSiZrCl$_2$ | 2100 | 10000:1 | 200 | 3.2 | 20[b] |
| rac-EBIOSiHfCl$_2$ | 200 | 10000:1 | 280 | 3.3 | 20[b] |
| rac-EBTHIOSiZrCl$_2$ | 2500 | 10000:1 | >1000 | 2-4 | 20[b] |
| rac-EBI*ZrCl$_2$ | 618000 | 10000:1 | 217 | 2.6 | This invention[c] |
| meso-EBI*ZrCl$_2$ | 382000 | 10000:1 | 202 | 2.5 | This invention[c] |
| rac-EBI*HfCl$_2$ | 12500 | 10000:1 | 227 | 2.9 | This invention[c] |
| meso-EBI*HfCl$_2$ | 33500 | 10000:1 | 103 | 3.0 | This invention[c] |

[a]50° C., $P_{C2}$ = 2 bar;
[b]40° C., $P_{C2}$ = 2.5 bar, IOSi = 2-OSiMe$_2$$^t$Bu-indenyl;
[c]70° C., $P_{C2}$ = 10 bar In general, Hf catalysts are less active than their Zr analogues, and polymers obtained with Hf catalysts show a higher molecular weight than the corresponding Zr species under similar conditions.[2-4] However, in the case of EBI*MCl$_2$, the meso Hf species seems unusual in this regard in that it has a dramatically lower $M_w$. The data in Table 11 show that the ansa bridged Ind species produce polymers with much lower $M_w$ than the unbridged analogues. The values of $M_w$ for the polymers produced by rac-EBIZrCl$_2$ and rac-EBI*ZrCl$_2$ are similar, however the $M_w$ of the rac-EBI*HfCl$_2$ catalysed sample is also lower than anticipated, despite being greater than its Zr catalysed analogue. It has been found that changing the catalyst type dramatically affects the $M_w$, with $M_w$ values increasing in the order EBIZrCl$_2$<Cp$_2$ZrCl$_2$<Cp$_2$HfCl$_2$<Cp$_2$TiCl$_2$<EBTHIZrCl$_2$.[17] Furthermore, the same study found increases in MAO concentrations to decrease average molecular weight. It is not unexpected therefore that the $M_w$ values for the EBI* species studied are the lowest in Table 11.

REFERENCES

1 D. O'Hare, J. C. Green, T. Marder, S. Collins, G. Stringer, A. K. Kakkar, N. Kaltsoyannis, A. Kuhn, R. Lewis, et al., *Organometallics*, 1992, 11, 48.

2. K. Weiss, U. Neugebauer, S. Blau, H. Lang, *J. Organomet Chem.*, 1996, 520, 171.

3. G. Jany, M. Gustafsson, T. Repo, E. Aitola, J. A. Dobado, M. Klinga, M. Leskela, *J. Organomet. Chem.*, 1998, 553, 173.

4. H. G. Alt, K. Fottinger, W. Milius, *J. Organomet. Chem.*, 1998, 564, 109.

5. C. Janiak, U. Versteeg, K. C. H. Lange, R. Weimann, E. Hahn, *J. Organomet. Chem.*, 1995, 501, 219.

6. P. C. Möhring, N. J. Coville, *Coord. Chem. Rev.*, 2006, 250, 18.

7. W. Kaminsky, R. Engehausen, K. Zoumis, W. Spaleck, J. Rohrmann, *Makromol. Chem.*, 1992, 193, 1643.

8. J. Tian, B. Huang, *Macromol. Rapid Commun.*, 1994, 15, 923.

9. A. E. Hamielec, J. B. P. Soares, *Prog. Polym. Sci.*, 1996, 21, 651.

10. F. Silveira, L. M. T. Simplicio, Z. Novais da Rocha, J. H. Zimnoch dos Santos, *Appl. Catal., A,* 2008, 344, 98.

11.1. M. Lee, W. J. Gauthier, J. M. Ball, B. Iyengar, S. Collins, *Organometallics,* 1992, 11, 2115.

12. G. J. P. Britovsek, V. C. Gibson, D. F. Wass, *Angew. Chem., Int. Ed. Engl.,* 1999, 38, 428.

13. J. C. W. Chien, D. He, *J. Polym. Sci., Part A: Polym. Chem.,* 1991, 29, 1585.

14. L. Izzo, L. Caporaso, G. Senatore, L. Oliva, *Macromolecules,* 1999, 32, 6913.

15. G. Melillo, L. Izzo, M. Zinna, C. Tedesco, L. Oliva, *Macromolecules,* 2002, 35, 9256.

16. R. Leino, H. J. G. Luttikhedde, P. Lehmus, C.-E. Wilen, R. Sjoeholm, A. Lehtonen, J. V. Seppaelae, J. H. Naesman, *Macromolecules,* 1997, 30, 3477.

17. L. D'Agnillo, J. B. P. Soares, A. Penlidis, *Macromol. Chem. Phys.,* 1998, 199, 955.

18. Janiak, C.; Versteeg, U.; Lange, K. C. H.; Weimann, R.; Hahn, E. *J. Organomet. Chem.* 1995, 501, 219-34.

19. G. Jany, M. Gustafsson, T. Repo, E. Aitola, J. A. Dobado, M. Klinga, M. Leskela, *J. Organomet. Chem.,* 1998, 553, 173.

20. R. Leino, H. J. G. Luttikhedde, P. Lehmus, C.-E. Wilen, R. Sjoeholm, A. Lehtonen, J. V. Seppaelae, J. H. Naesman, *Macromolecules,* 1997, 30, 3477.

21. Cosier, J.; Glazer, A. M. *J. Appl. Cryst* 1886, 19, 105-197.

22. *Processing of X-ray Diffraction Data Collected in Oscillation Mode*; Otwinowski, Z.; Minor, W., Eds.; Academic Press, 1997; Vol. 276.

23. Altomare, A.; Cascarano, G.; Giacovazzo, C.; Guagliardi, A.; Burla, M. C.; Polidori, G.; Camalli, M. *J. Appl. Crystallogr.* 1994, 27, 435.

24. Betteridge, P. W.; Carruthers, J. R.; Cooper, R. I.; Prout, K.; Watkin, D. J. *J. Appl. Crystallogr.* 2003, 36, 1487.

25. Cooper, R. I.; Thompson, A. L.; Watkin, D. J. *J. Appl. Cryst.* 2010, 43, 1100-1107.

What is claimed is:

1. A compound of the formula I shown below

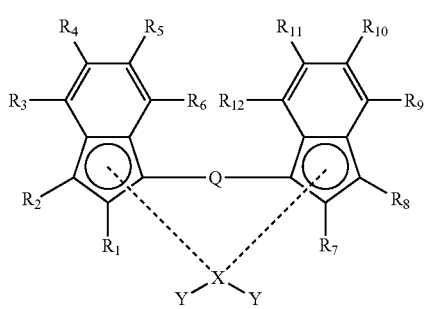

I wherein:

$R_1$, $R_2$, $R_3$, $R_4$, $R_5$, $R_6$, $R_7$, $R_8$, $R_9$, $R_{10}$, $R_{11}$ and $R_{12}$ are methyl;

Q is —$CH_2$—$CH_2$—;

X is zirconium, titanium or hafnium; and each Y group is selected from halo or a (1-2C)alkyl group which is optionally substituted with halo, phenyl, or Si[(1-4C)alkyl]$_3$.

2. The compound according to claim 1, wherein X is zirconium or hafnium.

3. The compound according to claim 1, wherein each Y group is the same.

4. The compound according to claim 1, wherein the compound has the structural formula:

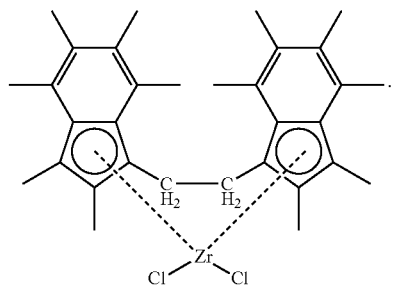

5. A process of preparing a compound according to claim 1, comprising:

(i) reacting a compound of formula A:

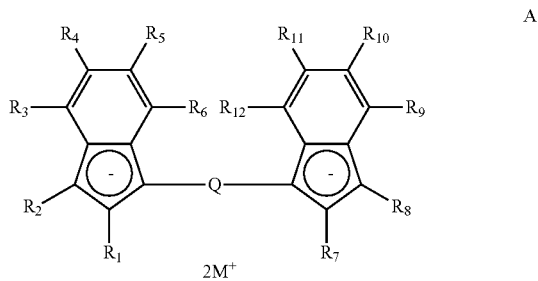

A wherein Q, $R_1$, $R_2$, $R_3$, $R_4$, $R_5$, $R_6$, $R_7$, $R_8$, $R_9$, $R_{10}$, $R_{11}$, and $R_{12}$ are each as defined in claim 1 and M is Li, Na or K;

with a compound of the formula B:

X(Y')$_4$     B wherein X is as defined in claim 1 and Y' is halo;

in the presence of a solvent to form a compound of formula Ia:

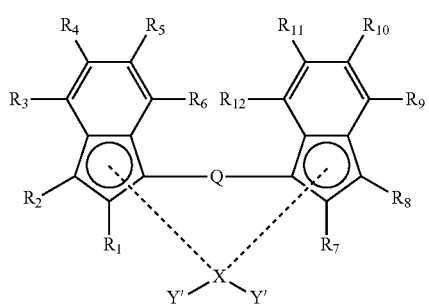

Ia and optionally thereafter:

(i) reacting the compound of formula Ia above with MY" (wherein M is Li, Na or K and Y" is a group Y as defined in claim 1 other than halo), in the presence of a suitable solvent to form a compound of formula Ib shown below

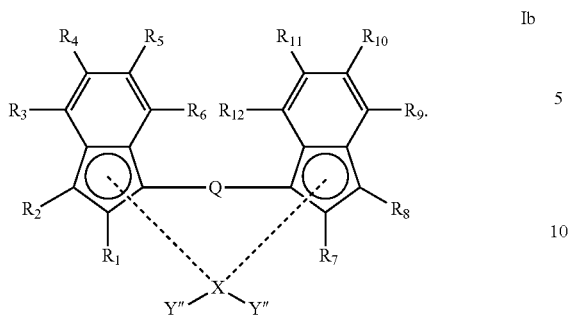

6. A procatalyst for the polymerization of ethene, comprising a compound of formula I according to claim 1 prepared according to the process of claim 5.

7. A process for forming a polyethylene which comprises reacting ethene monomers in the presence of a compound of formula I according to claim 1 and an activator.

8. A process according to claim 7, wherein the activator is an aluminoxane or triethylaluminium.

9. The process of claim 5, wherein Y' is chloro or bromo.

10. The process of claim 8, wherein the aluminoxane is methylaluminoxane.

* * * * *